(12) United States Patent
Kaneda

(10) Patent No.: US 7,803,621 B2
(45) Date of Patent: *Sep. 28, 2010

(54) VIRUS ENVELOPE VECTOR FOR GENE TRANSFER

(75) Inventor: Yasufumi Kaneda, Osaka (JP)

(73) Assignee: AnGes MG, Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/126,770

(22) Filed: May 10, 2005

(65) Prior Publication Data

US 2005/0239188 A1 Oct. 27, 2005

Related U.S. Application Data

(63) Continuation of application No. 09/937,839, filed as application No. PCT/JP01/00782 on Feb. 2, 2001, now Pat. No. 6,913,923.

(30) Foreign Application Priority Data

Feb. 2, 2000 (JP) ............................. 2000-025596

(51) Int. Cl.
*A61K 48/00* (2006.01)
*C12N 15/00* (2006.01)

(52) U.S. Cl. .................... 435/455; 424/93.2; 435/320.1

(58) Field of Classification Search ............. 435/320.1; 424/93.2, 93.1; 514/44
See application file for complete search history.

(56) References Cited

U.S. PATENT DOCUMENTS

| | | | |
|---|---|---|---|
| 4,266,024 A * | 5/1981 | Swetly et al. | 435/70.5 |
| 5,244,635 A * | 9/1993 | Rabson et al. | 422/72 |
| 5,683,866 A | 11/1997 | Sarkar et al. | |
| 5,843,459 A | 12/1998 | Wang et al. | |
| 5,846,707 A | 12/1998 | Roizman | |
| 5,849,561 A * | 12/1998 | Falck-Pedersen | 435/235.1 |
| 5,879,685 A | 3/1999 | Gluck et al. | |
| 6,020,202 A | 2/2000 | Jessee | |
| 6,051,428 A | 4/2000 | Fong et al. | |
| 6,183,752 B1 | 2/2001 | Epstein et al. | |
| 6,372,957 B1 | 4/2002 | Olson | |
| 6,432,925 B1 * | 8/2002 | Hoon et al. | 514/44 |
| 6,451,592 B1 | 9/2002 | Dubensky, Jr. et al. | |
| 6,472,375 B1 * | 10/2002 | Hoon et al. | 514/44 |
| 6,509,162 B1 | 1/2003 | Altieri | |
| 6,670,176 B1 * | 12/2003 | Samulski et al. | 435/320.1 |
| 6,913,923 B2 * | 7/2005 | Kaneda | 435/320.1 |

FOREIGN PATENT DOCUMENTS

| | | |
|---|---|---|
| EP | 0 555 333 B1 | 12/1995 |
| WO | WO 95/16784 A1 | 6/1995 |

OTHER PUBLICATIONS

Ramani et al PNAS 95:11886-11890, 1998.*
Ramani K, Site-specific gene delivery in vivo through engineered Sendai viral envelopes, 1998, PNAS, vol. 95, pp. 11886-11890.*
Paternostre M, Solubilization and reconstitution of vesicular stomatitis virus envelope using octylglucoside, 1997, Biophysical J., vol. 72, pp. 1683-1694.*
Kaneda et al. Increased expression of DNA cointroduced with nuclear protein in adult rat liver, 1989, Science, vol. 243, pp. 375-378.*
Liu et al., 1995, J. of Immunology, vol. 154, pp. 3147-3155.*
Liu et al.,1995, J. of Immunology, vol. 154, pp. 3147-3155.*
Ramani et al., 1998, PNAS, vol. 95, pp. 11886-11890.*
Bagai et al., 1993, J. Virology, vol. 67(6) pp. 3312-3318.*
Lee et al., *Virology* 128:65-76, 1983.
Microbiology & Immunology: BS3035: Paramyxoviruses [online], Jan. 21, 2003 [retrieved on Apr. 9, 2003]. Retrieved from the Internet:<URL:http://www-micro.msb.le.ac.uk/3035paramyxoviruses.html>.
Swaney et al., *Gene Therapy* 4:1379-1386, 1997.
Ramani, K. et al., "Novel gene delivery to liver cells using engineered virosomes," *FEBS Letters* 404, pp. 164-168, 1997.
Vlasov, V. et al., "The efficient method for DNA incorporation into reconstituted Sendai virus envelopes," *Chemical Abstracts*, 109(25):411, abstract 226002h(1988), abstract only.
Fields, B.N. et al., *Virology*, Lipincott Williams & Wilkins, pp. 1177-1204, 1996.
Harmsen, M.C. et al., "Reconstitution and Fusogenic Properties of Sendai Virus Envelopes", *Eur J. Biochem*, vol. 149, No. 3, pp. 591-600, 1985.
Chin, Andrew, "On the Preparation and Utilization of Isolated and Purified Oligonucleotides", Mar. 9, 2002 (sequence listing on CD-ROM).
Mulligan, *Science* 260:926-932, 1993.
Ledley, *Human Gene Therapy*, 6:1129-1144, 1995.
Cole, G. A. et al., *J Immunology* 158:4301-4309, 1997.
Uchida, T. et al., *J. Cell Biol.* 80:10-20, 1979.
Dzau, V.J. et al., *Proc. Natl. Acad. Sci USA* 93:11421-11425, 1996.
Kaneda, Y. et al., *Molecular Medicine Today* 5:298-303, 1999.
Okada, Y. et al., *Biken Journal* 4:209-213, 1961.
Bagai, S. et al., *Journal of Virology* 67(6):3312-3318, 1993.
Wainberg, et al., *Applied Microbiology*, 22(4):618-621, 1971.
Mabuchi et al., *Gene Therapy*, 4:768-772 (1997).
Clarke, P. and Clements, J.B. "Mutagenesis occurring following infection with herpes simplex virus does not require virus replication", *Virology*, 182:597-606 (1991).

(Continued)

*Primary Examiner*—Peter Paras, Jr.
*Assistant Examiner*—David Montanari
(74) *Attorney, Agent, or Firm*—Foley & Lardner LLP

(57) ABSTRACT

A gene transfer vector is prepared by introducing an exogenous gene into an inactivated virus envelope, through a freezing and thawing treatment or mixing with a detergent. There are also provided a pharmaceutical composition for gene therapy containing this gene transfer vector, a kit containing this gene transfer vector, and a gene transfer method employing this gene transfer vector.

17 Claims, 29 Drawing Sheets

OTHER PUBLICATIONS

Neuwelt, E.A. et al. "Delivery of ultraviolet-inactivated 35S-herpesvirus across an osmotically modified blood-brain barrier", *Journal of Neurosurgery*, 74(3):475-479 (1991).

Cotten et al., "Psoralen Treatment of Adenovirus Particles Eliminates Virus Replication and Transcription While Maintaining the Endosomolytic Activity of the Virus Capsid", *Virology*, 205254-261 (1984).

Hangai et al., "In Vivo Delivery of Phosphorothioate Oligonucleotides Into Murine Retina", *Arch Ophthalmol.*, 116:342-348 (1998).

Kim et al. "Effect of Lipid Compositions on Gene Transfer into 293 Cells Using Sendai F/HN-Virosomes", *Journal of Biochemistry and Molecular Biology*, 35(5):459-464 (2002).

Nakanishi et al., "Glycoproteins of Sendai Virus (HVJ) Have A Critical Ratio for Fusion Between Virus Envelopes and Cell Membranes", *Exp Cell Research*, pp. 143-151(1982).

Nakanishi et al., "Preparation of Unilamellar Fusogenic Liposomes Using the Sendai Virus", *Folia Pharmacol. Jpn.*, 112:299-305 (English Abstract) (1998).

Otsuji et al., "In Vivo Gene Transfer into Choroidal Neovascularization by the HVJ Liposome Method", *Graefe's Arch Clin Exp Ophthalmol*, 238:191-199 (2000).

Race et al., "A Multistep Procedure for the Chemical Inactivation of Human Immunodeficiency Virus for Use as an Experimental Vaccine", *Vaccine*, 13(15):1567-1575 (1995).

Saeki et al., "Development and Characterization of Cationic Liposomes Conjugated with HVJ (Sendai Virus): Reciprocal Effect of Cationic Lipid for In Vitro and In Vivo Gene Transfer", *Human Gene Therapy*, 8:2133-2141 (1997).

Vainstein et al., "A New Method for Reconstitution of Highly Fusogenic Sendai Virus Envelopes", *Biochimica et Biophysica ACTA*, 773:184-188 (1984).

Kwong et al., *Journal of Virology*, 51:595-603 (1984).

\* cited by examiner

=100nm

Infection time and protamine sulfate concentration

Infection time and protamine sulfate concentration 60 min 60 min 10 min 10 min

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
ccttgaaggg atttccctcc                                            20

<210> SEQ ID NO 2
<211> LENGTH: 27
<212> TYPE: DNA
<213> ORGANISM: Artificial Sequence
<220> FEATURE:
<223> OTHER INFORMATION: synthetic

<400> SEQUENCE: 2
gatcaagacc ttttcccaag aatctat                                    27
```

```
<210> SEQ ID NO 3
<211> LENGTH: 27
<212> TYPE: DNA
<213> ORGANISM: Artificial Sequence
<220> FEATURE:
<223> OTHER INFORMATION: synthetic

<400> SEQUENCE: 3
catgttctgg aaaagggttc ttagata                                          27
```

VIRUS ENVELOPE VECTOR FOR GENE TRANSFER

This application is a continuation of U.S. application Ser. No. 09/937,839 now U.S. Pat. No. 6,913,923 filed Feb. 21, 2002, which claims priority to PCT/JP01/00782, filed Feb. 2, 2001, now publication no. WO 01/57204, published Aug. 9, 2001, which claims priority to Japanese Application No. 2000-25596, filed Feb. 2, 2000, all of which are incorporated herein by reference in their entirety.

TECHNICAL FIELD

The present invention relates to a safe and high-efficiency vector for in-vitro and in-vivo gene transfer. In particular, the present invention relates to a gene transfer vector which is prepared by using a virus or an inactivated virus, in particular inactivated HVJ (Sendai virus). Moreover, the gene transfer vector described in the present specification can also be used for gene therapy and high throughput screening.

BACKGROUND ART

A number of viral and non-viral (synthetic) methods for gene transfer have been developed that are intended for gene therapy (Mulligan, Science, 260, 926 to 932(1993) and Ledley, Human Gene Therapy, vol. 6, 1129 to 1144(1995)). In general, viral methods are more effective than non-viral methods for gene delivery into cells. However, viral vector may present safety concerns due to the concurrent introduction of essential gene elements from the parent virus, leaky expression of viral genes, immunogenicity, and modification of the host genome structure. In general, a non-viral vector has less cytotoxicity and less immunogenicity. However, a majority of non-viral methods have a lower gene transfer efficiency, esp. in vivo, than some viral vectors.

Thus, both virus vectors and non-viral vectors have limitations as well as advantages. Therefore, a high-efficiency and low-toxicity gene transfer vector for in vivo use must be developed so as to compensate for the limitations of one type of vector system with the advantages of another type of system.

On the other hand, HVJ has high immunogenicity, and is known to induce CTL especially when NP protein is produced in a large quantity (Cole, G. A. et al., J. Immunology 158, 4301 to 4309(1997)). It is also feared that the protein synthesis by the host may be inhibited.

HVJ also has a problem in that particles which are created by a method in which a fusion protein is purified by subjecting the virus fusion protein to centrifugation or column manipulation so as to be reconstituted on a lipid membrane may lose the other proteins (primarily M protein) of the virus due to the reconstitution, so that the ratio between the F1 which is required for fusion activity and the HN protein cannot be maintained at the same level as that of the wild-type virus, resulting in a lower fusion activity. Moreover, since the orientation in which the fusion protein is inserted into the lipid membrane at the time of reconstitution may not necessarily be the same as in the wild-type virus, some unknown antigens may be presented.

A method has also been reported in which reconstitution is carried out by adding new molecules (Uchida, T. et al., J. Cell. Biol. 80, 10 to 20, 1979). However, this method runs a high risk of losing the original viral functions because the membrane composition of the completed particles is substantially different from that of the native virus particles.

Methods which involve encapsulating genes or proteins in liposomes and fusing this with inactivated HVJ to create fusion particles, as in conventional HVJ-liposome, have enabled a non-invasive gene transfer into cultured cells or in vivo tissue. This technique is in frequent use worldwide at the animal experimentation level (Dzau, V. J. et al., Proc. Natl. Acad. Sci. USA, 93, 11421 to 11425(1996) and Kaneda, Y. et al., Molecular Medicine Today, 5, 298 to 303(1999)). However, it has also been found that this technique has drawbacks: for example, the procedure may be complicated because two different vesicles, i.e., a virus and a liposome must be prepared; the particles whose average diameter has increased to be 1.3 times that of viral particles due to fusion with the liposome have a fusion activity which is 10% or less of that of the virus.

Furthermore, with respect to some tissue, vectors based on conventional HVJ may not be able to achieve any gene transfer, or if at all they do, with an extremely low efficiency. This indicates that the tissue for gene therapy based on conventional methods may be limited.

There is a desire for the development of a viral vector for human gene therapy, which can be prepared safely, highly efficiently, and simply, and yet enables gene transfer to a broad range of in vivo tissue.

Therefore, an objective of the present invention is to develop a safe, highly efficient, and simple virus-based gene transfer vector for a broad range of cultured cells or in vivo tissue which can overcome the drawbacks of conventional reconstituted HVJ vector methods or HVJ-liposome methods.

DISCLOSURE OF THE INVENTION

In one aspect of the present invention, a safe and highly efficient gene transfer vector which utilizes an inactivated virus is provided. An inactivated virus, in which the genome of the virus has been inactivated, does not replicate virus proteins, and therefore is safe and has low cytotoxicity and low antigenicity. By encapsulating a gene in a virus envelope vector, which is a gene transfer vector utilizing an inactivated virus, a safe, highly efficient, and simple gene transfer vector for cultured cells or in vivo tissue can be prepared.

In a further aspect of the present invention, a virus envelope vector which is capable of gene transfer into a broad range of in vivo tissue is provided. In one embodiment, the virus used is HVJ. Examples of the tissue to which gene transfer can be achieved in vivo by using the virus envelope vector according to the present invention include, without limitation: the liver, skeletal muscles, the uterus, brain, eyes, carotid arteries, skin, blood vessels, the lung, the heart, kidneys, the spleen, cancer tissue, nerves, B lymphocytes, and respiratory tract tissue.

In another aspect of the present invention, method for simply realizing gene transfer to suspended cells is provided. Examples of preferable gene transfer methods to suspended cells which use the virus envelope vector according to the present invention include a gene transfer method which includes the steps of mixing suspended cells with the virus envelope vector in the presence of protamine sulfate, and applying a centrifugal force to the mixture.

In one aspect of the present invention, a highly efficient and rapid gene transfer to cultured cells and in vivo tissue is realized by utilizing the gene transfer vector according to the present invention to encapsulate a large quantity of genes in a short period of time. Therefore, in a further aspect of the present invention, a high-throughput, quick mass analysis system for genome which utilizes the gene transfer vector according to the present invention is realized.

In a particular aspect of the present invention, a gene transfer vector can be stored for a long period of time (at least two to three months or more) in a frozen state at −20° C. This gene transfer vector can be sealed, stored, and transported in a frozen state, for example.

In another aspect of the present invention, a gene transfer vector is provided which has a gene transfer activity, in vitro, for preferably 70% or more cells, more preferably 80% or more cells, still more preferably 90% or more cells, and most preferably 95% or more cells.

In a certain aspect of the present invention, a gene transfer vector is provided which, in the case where a virus envelope vector is created as a gene transfer vector in two months after an inactivated virus is prepared, maintains a gene transfer activity of 60% or more, preferably 70% or more, more preferably 80% or more, most preferably 90% or more.

In another aspect of the present invention, a gene transfer vector is provided which, in a local administration in vivo, has a gene transfer activity for preferably 30% or more cells in tissue, more preferably 40% or more cells in tissue, still more preferably 50% or more cells in tissue, and most preferably 60% or more cells in tissue.

In an aspect of the present invention, a gene transfer vector containing an inactivated virus envelope is provided.

In one aspect of the present invention, the virus which is used for the preparation of the gene transfer vector may be a wild-type virus or a recombinant-type virus.

In a further aspect of the present invention, the virus used is a virus belonging to a family selected from the group consisting of: Retroviridae, Togaviridae, Coronaviridae, Flaviviridae, Paramyxoviridae, Orthomyxoviridae, Bunyaviridae, Rhabdoviridae, Poxyiridae, Herpesviridae, Baculoviridae, and Hepadnaviridae. In a particular aspect of the present invention, the virus used is HVJ. In a further aspect of the present invention, a gene transfer vector is prepared by using a recombinant-type Sendai virus described in Hasan, M. K. et al. (Journal of General Virology, 78, 2813 to 2820(1997)) or Yonemitsu, Y. et al. (Nature Biotechnology 18, 970 to 973 (2000)).

In another aspect of the present invention, a gene transfer vector for achieving gene transfer to animal in vivo tissue is provided.

In a method for preparing the gene transfer vector according to the present invention, it is not necessary to perform a step of inactivating a virus. Therefore, in one aspect of the present invention, without performing a step of inactivating a virus, a gene transfer vector can be prepared by a method which includes the steps of:
  1) mixing a virus with an exogenous gene, and
  2) freezing and thawing the mixture, or further mixing the mixture with a detergent.

In another aspect of the present invention, a method for preparing an inactivated virus envelope vector for gene transfer is provided, the method including the steps of:
  inactivating a virus,
  mixing the inactivated virus with an exogenous gene, and
  freezing and thawing the mixture.

In a further aspect of the present invention, a method for preparing an inactivated virus envelope vector for gene transfer is provided, the method including the steps of:
  inactivating a virus, and
  mixing the inactivated virus with an exogenous gene in the presence of a detergent.

In a further aspect of the present invention, the detergent used is selected from the group consisting of octylglucoside, Triton-X100, CHAPS and NP-40.

In a particular aspect of the present invention, a method for preparing an inactivated virus envelope vector is provided, the method further including a step of adding a protamine sulfate to the exogenous gene before being mixed with an inactivated virus envelope.

In a further aspect of the present invention, a method for introducing a gene into isolated animal tissue is provided, the method including the steps of:
  preparing a gene transfer vector including a desired gene, and
  introducing a gene into the animal tissue via a gene transfer vector.

In another aspect of the present invention, a method for introducing an exogenous gene into suspended cells is provided, the method including the steps of:
  mixing suspended cells and a gene transfer vector in the presence of protamine sulfate, and
  centrifuging the mixture.

In still another aspect of the present invention, a pharmaceutical composition for gene therapy including the gene transfer vector according to the present invention is provided.

BRIEF DESCRIPTION OF THE DRAWINGS

FIGS. 10A-1 to 10A-3 and 10B-1 to 10B-3 are graphs representing gene transfer efficiency represented in terms of luciferase activity levels which were taken at the respective protamine sulfate (PS) concentrations and the respective transfection times, as shown in the figures.

FIGS. 11A-1 to 11A-2 and 11B are graphs representing gene transfer activity levels which were taken at the respective DNA amounts (amounts used in the experiment), and the respective storage temperatures, as shown in the figures.

FIGS. 16D-1 to 16D-3 show the results of administering HVJ envelope vectors containing pEGFP-1 of 10,000 HAU to DS rats (male, body weight: 300 to 400 g) via the cisterna magna or via the carotid artery. Three to four days after the administration, the rats were sacrificed, and live sections were prepared, which were subjected to observation under fluorescence microscopy.

FIG. 16D-1: administration via the cisterna magna.

Gene introduction into the brain surface was confirmed. On the other hand, no gene transfer into deep portions of the brain was confirmed. No gene transfer into the choroid plexus was confirmed, either.

Figure 2:
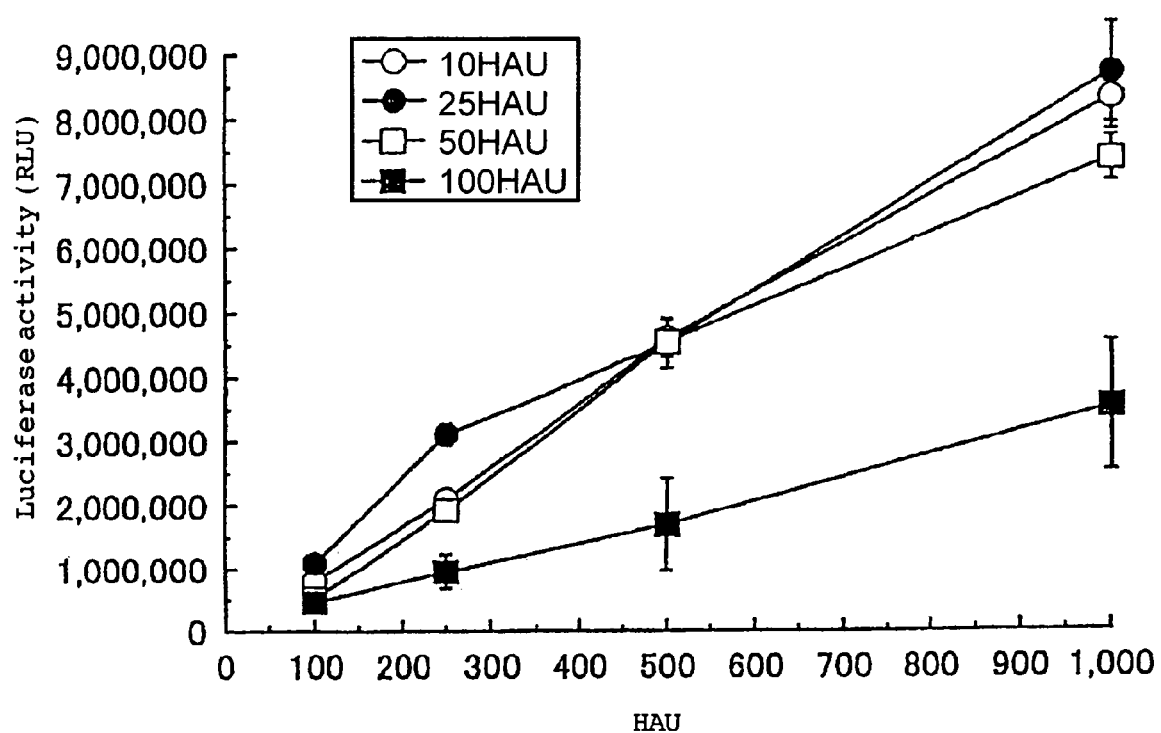
FIG. 2 shows results of luciferase activity measurement in the case where cultured cells were transfected, ensuring that the same number of viruses were employed for the preparation of an HVJ envelope vector to be added to the cultured cells.
Figure 3:
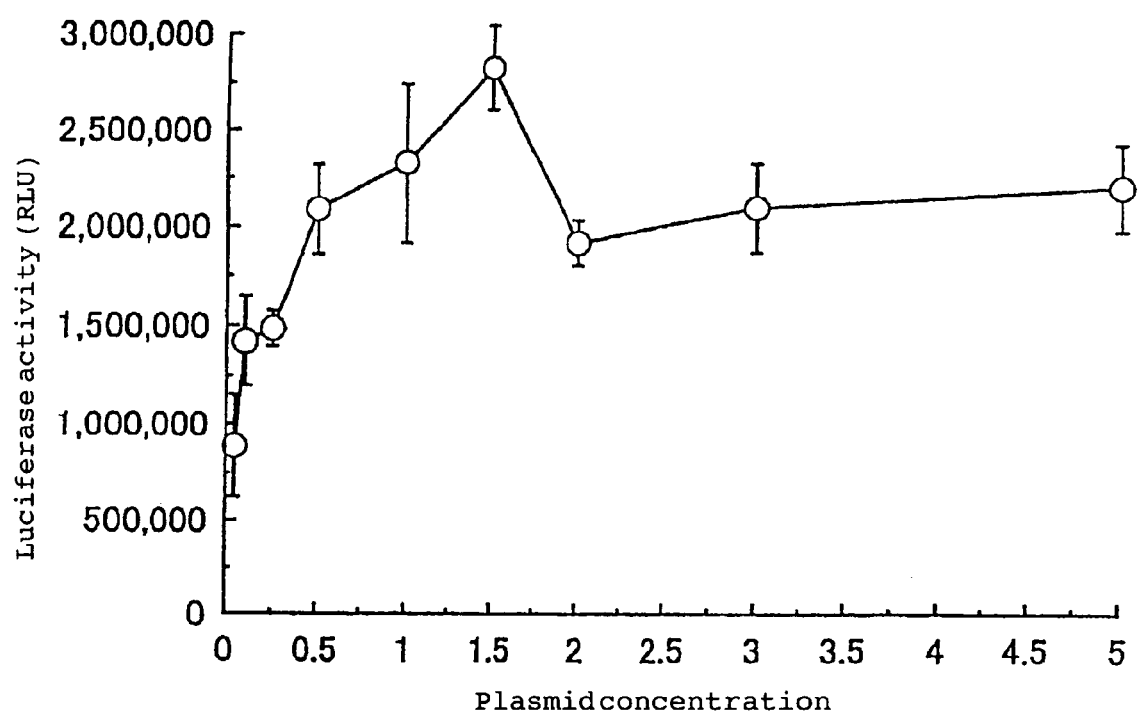
FIG. 3 shows results of luciferase activity measurement in the case where various amounts of an exogenous gene (luciferase expression vector) was employed in the HVJ envelope vector.
Figure 16A:
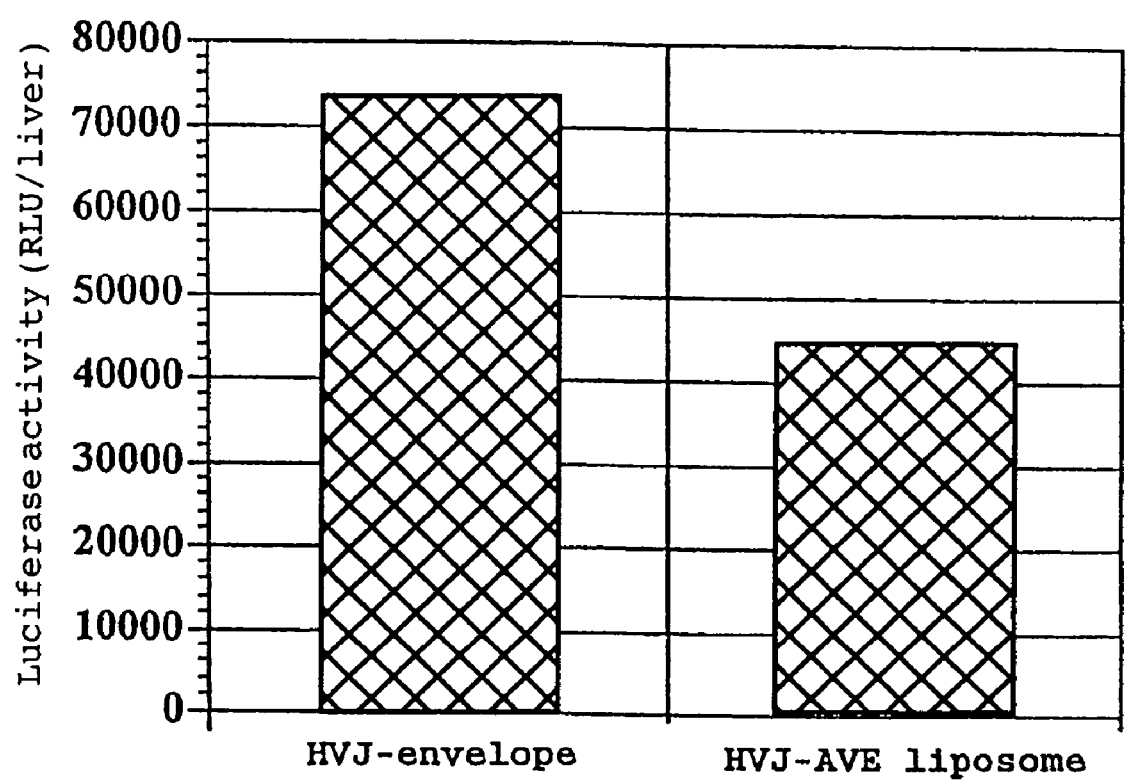
FIG. 16A is a graph representing gene transfer efficiency, for mouse livers, represented in terms of luciferase activity levels which were taken by employing the HVJ envelope vector according to the present invention or HVJ-AVE (Artificial Viral Envelope) liposome.
Figure 16B:
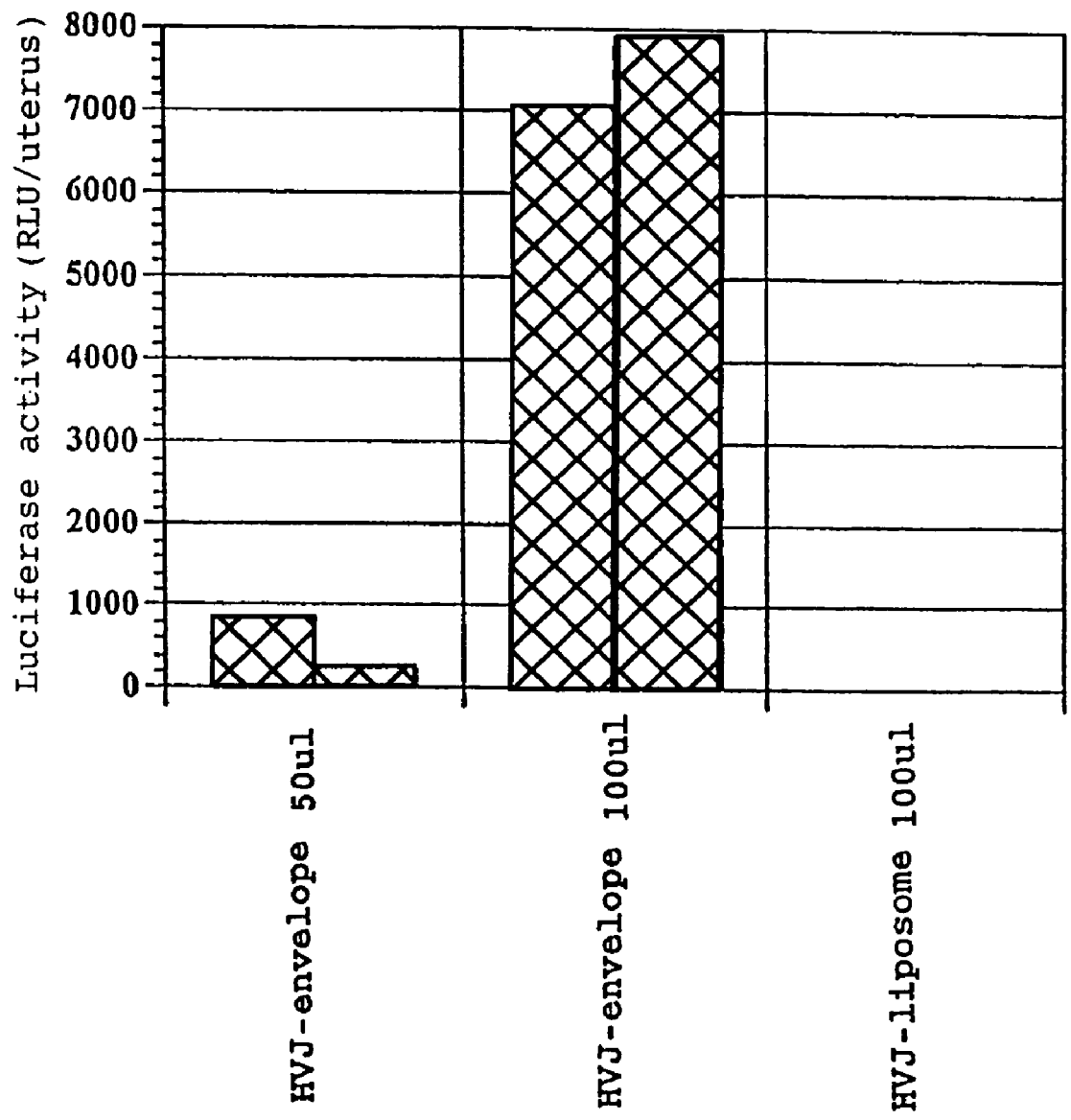
FIG. 16B is a graph representing gene transfer efficiency, for mouse uteri, represented in terms of luciferase activity levels which were taken by employing the HVJ envelope vector according to the present invention or HVJ-AVE (Artificial Viral Envelope) liposome.
Figure 16C:
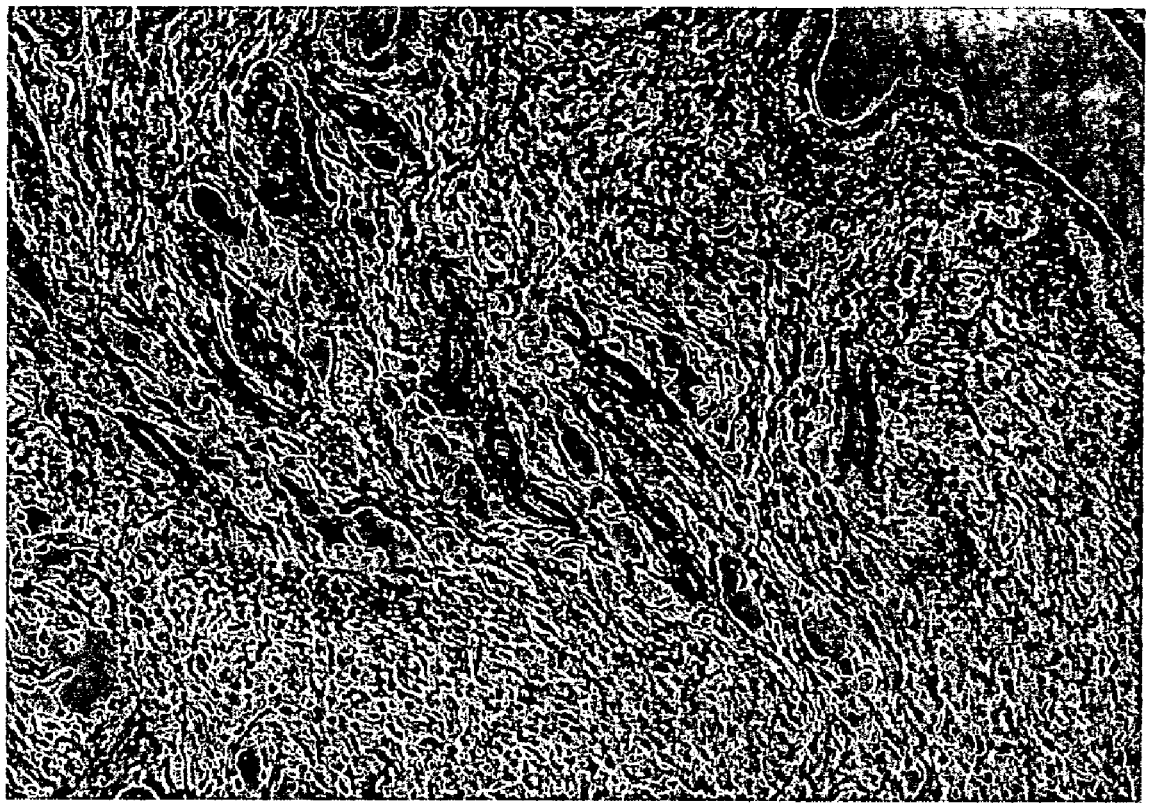
FIG. 16C shows results of LacZ staining for uterus tissue which was performed after the pEB-CMV-LacZ gene transfer employing the HVJ envelope vector according to the present invention for mouse uteri. Through LacZ staining, expression of the LacZ gene was detected chiefly in the glandular epithelium of the endometrium.
Figures 1, 16D:
Figures 2, 16D:
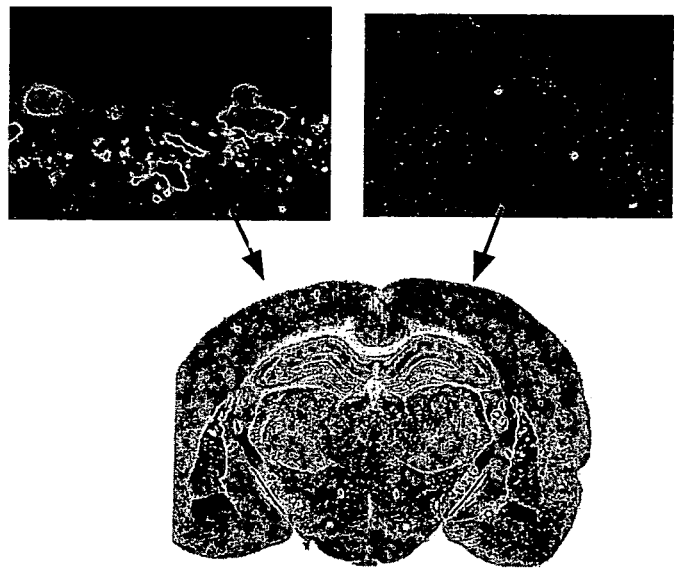
Figures 3, 16D:
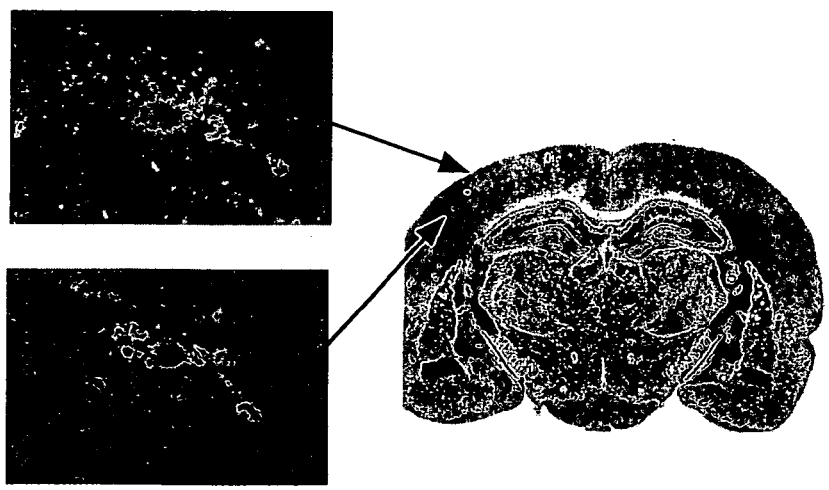

FIGS. 16D-2 and 16D-3: administration via the carotid artery.

A significantly high expression was confirmed on the left side, where administration was carried out. Expression was confirmed not only in the brain surface portions but also in the basal ganglia portion, and also in the brain surface of the other brain. The expression in the brain surface of the other brain was considered to have flowed to the other side through a collateral flow.

Figure 16E:
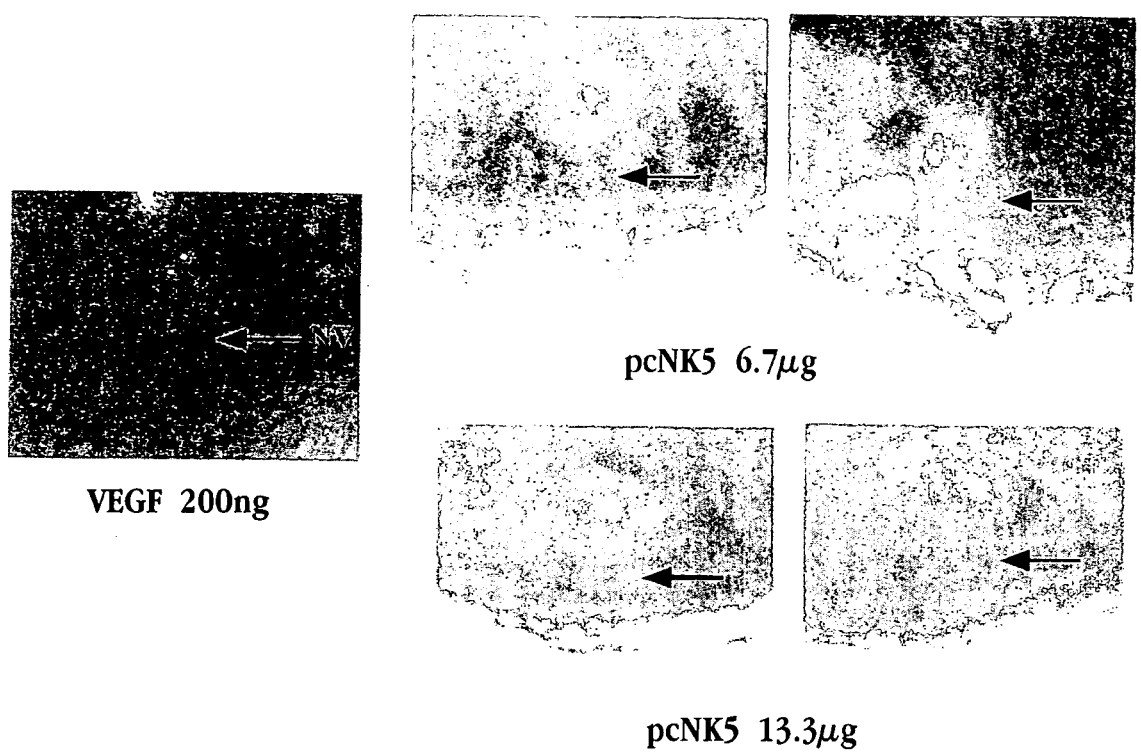

FIG. 16E shows results of dose-dependant suppression of VEGF-induced angiogenesis by pCMV-NK4, which is a vector which expresses a mutant HGF which inhibits the HGF function.

Figure 16F:
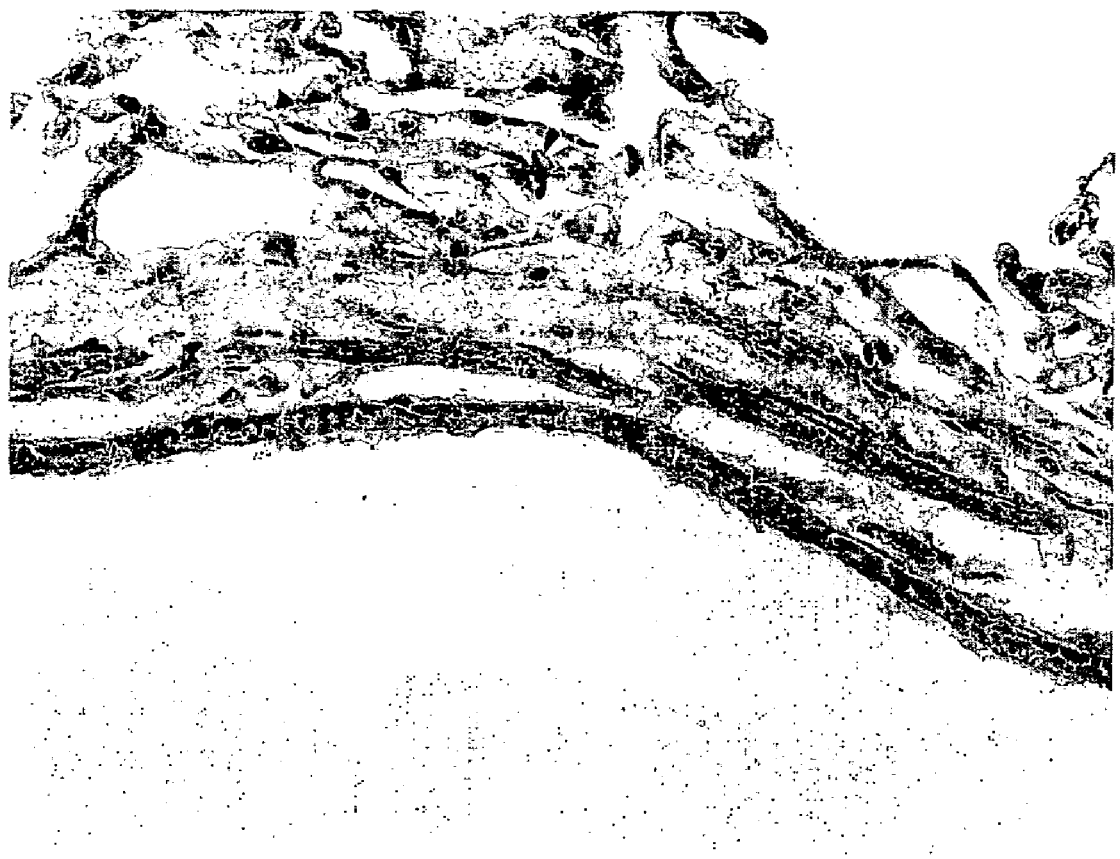

FIG. 16F shows results of gene transfer which was carried out by injecting an HVJ envelope vector into the trachea.

Figure 1:
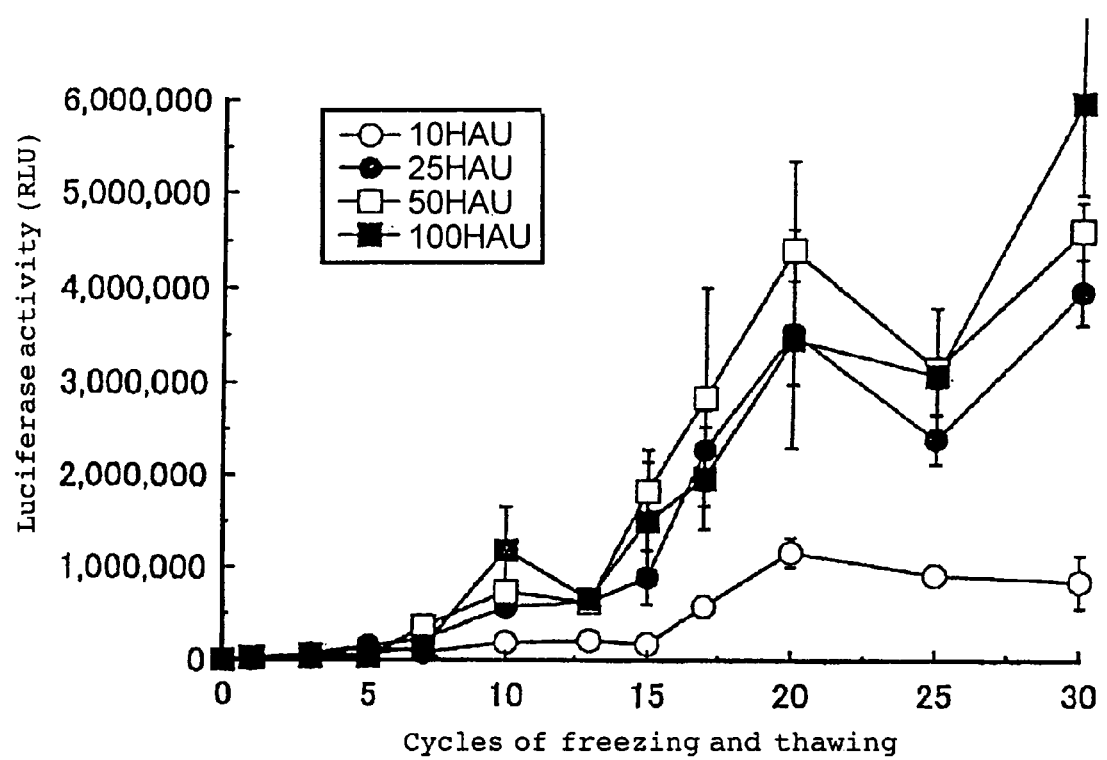
FIG. 1 shows the results of measurements of the expression level (luciferase activity) of an exogenous gene (luciferase gene), after freezing and thawing an HVJ envelope vector various numbers of times and transfecting cultured cells.
Figures 1, 17A:
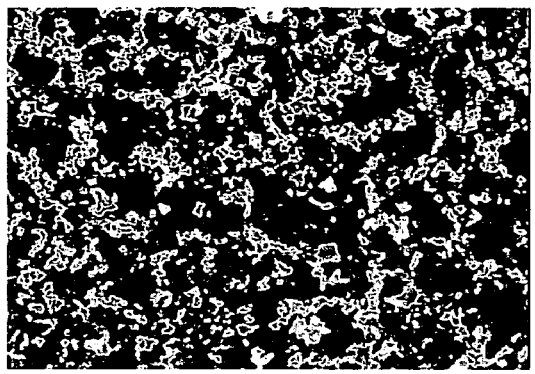
Figures 2, 17A:
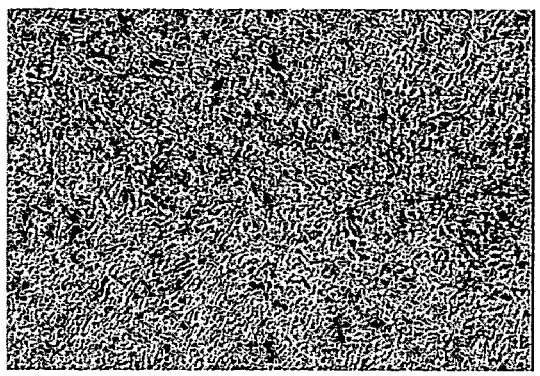

FIGS. 17A-1 to 17A-2 and 17B-1 to 17B-2 show results of cell fluorescence observed under fluorescence microscopy on the next day of introduction of oligonucleotides into cells. About 10% oligonucleotide introduction efficiency was obtained after 10 minutes of incubation (FIG. 17B-1 and 17B-2), whereas the oligonucleotides were introduced into 80% or more of the cells after 60 minutes of incubation (FIG. 17A-1 and 17A-2).

Figure 18A:
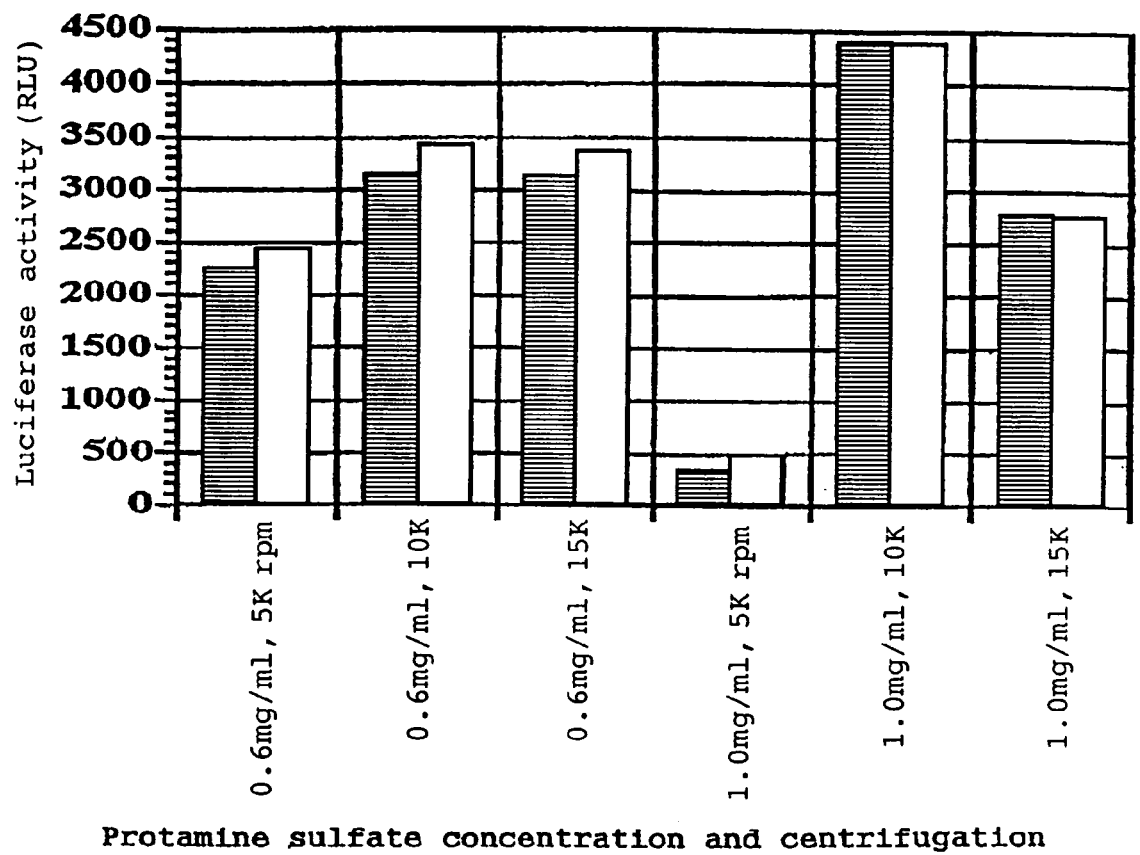
Figure 18B:
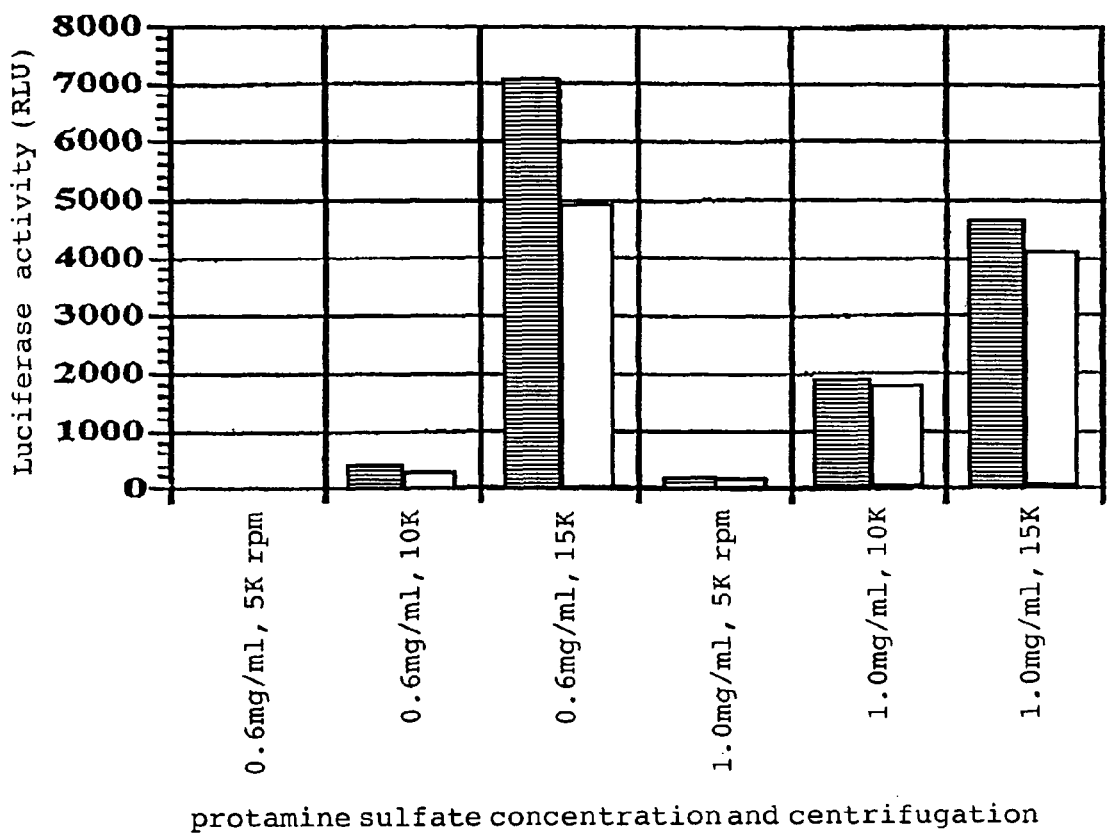
Figure 18C:
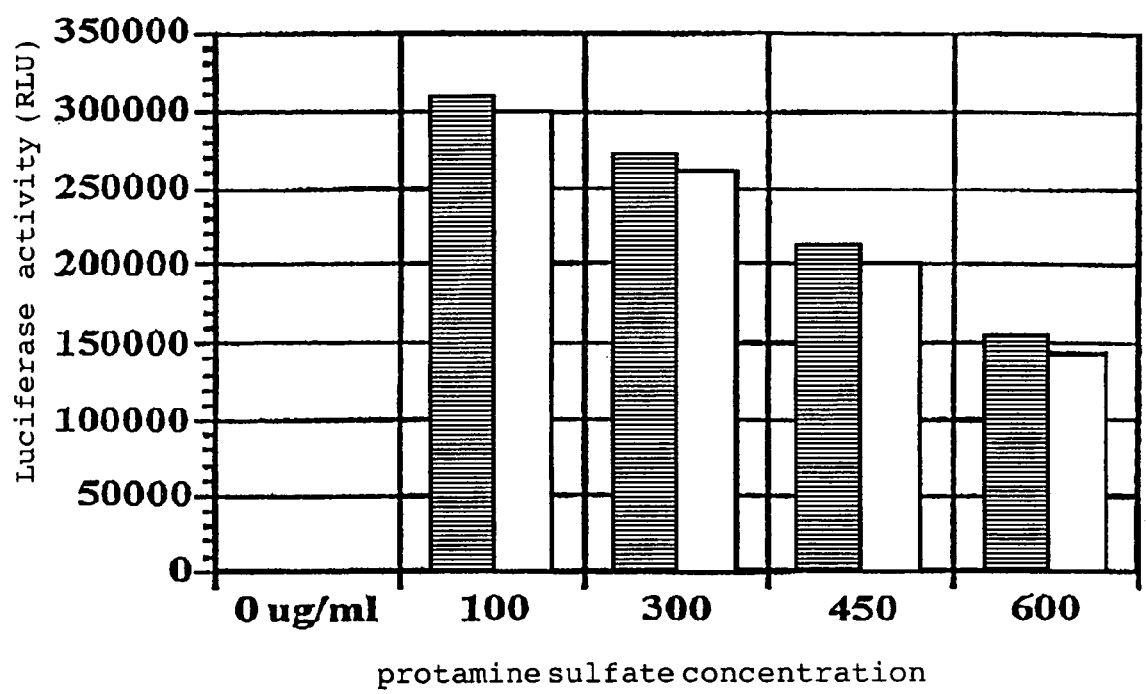

FIGS. 18A-18C show the results of an introduction experiment on CCRF-CEM (FIG. 18B), NALM-6 (FIG. 18A), and K-562 (FIG. 18C), which are human leukemia cell lines.

These cell lines (in particular CCRF-CEM and NALM-6) would show a very low introduction efficiency in the case where HVJ-liposome or existing liposome reagents (Lipofectamine, Lipofectin and the like of Gibao BRL) are used.

High luciferase activity was obtained under the following conditions: addition of 600 to 1,000 μg/ml of protamine sulfate and a centrifugation at 10,000 rpm or 15,000 rpm, for 10 minutes at 20° C. No significant cytotoxicity associated with the HVJ envelope vector was observed. Both centrifugation and the addition of protamine sulfate were required for the gene transfer.

Figure 19:
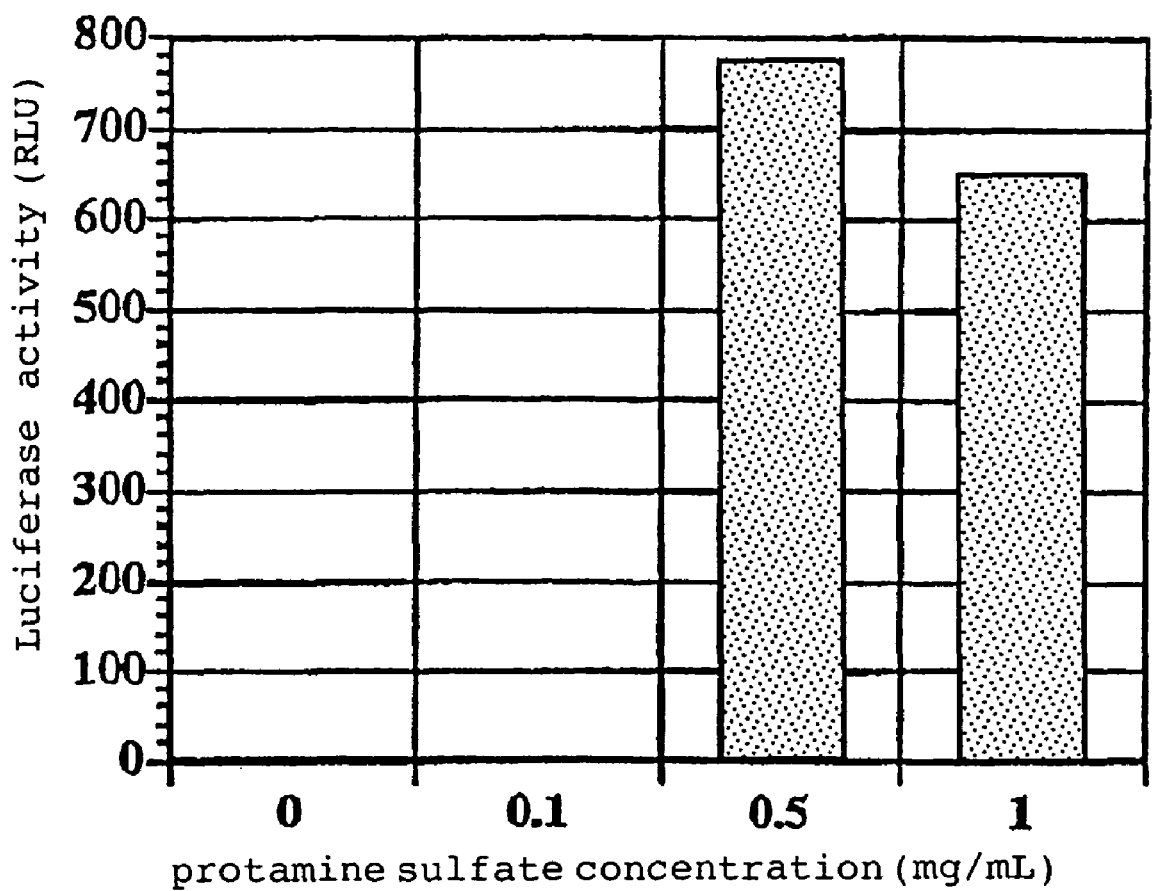

FIG. 19 shows results of gene transfer to cancerous tissue. Gene expression was observed in a tumor mass which is cancerous tissue. In particular, a high gene transfer activity was obtained with 500 μg/ml of protamine sulfate. On the other hand, gene expression was not detectable at lower protamine sulfate concentrations.

Figure 20:
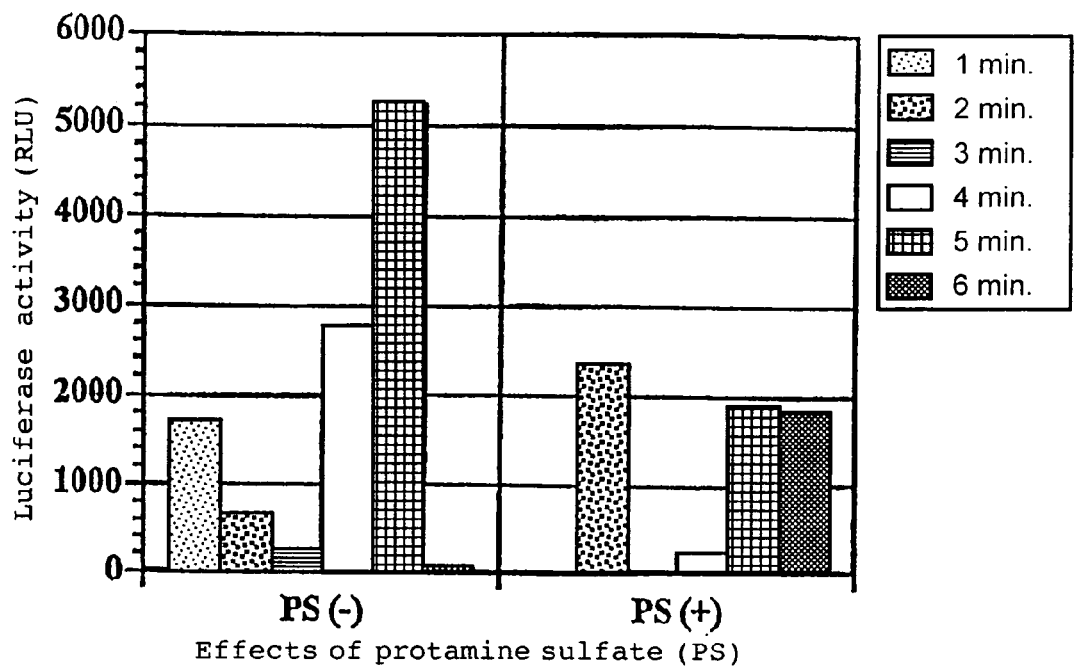

FIG. 20 shows results of gene transfer to cells employing a herpes virus envelope vector. Although the total luciferase activity was low, it was determined that a vector having the highest introduction efficiency was obtained through a treatment with Triton-X10 for 5 minutes. A preparation method which did not employ protamine sulfate had a high introduction efficiency. None of the samples showed any cytotoxicity through a morphological observation.

Figure 21:
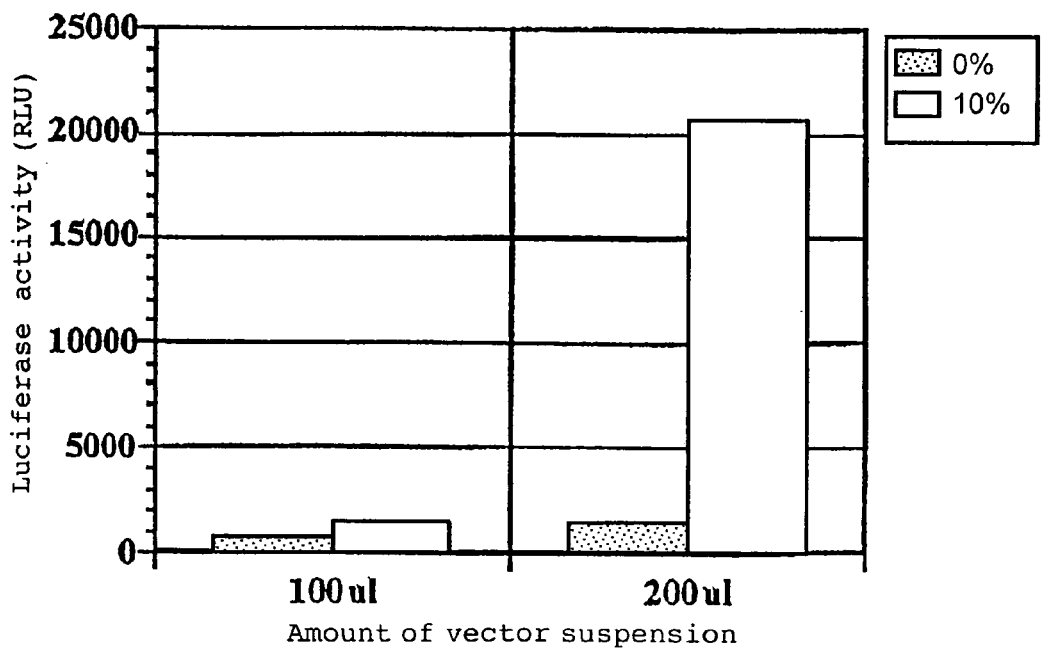

FIG. 21 shows results of gene transfer to cells with a herpes virus envelope vector which had been stored at −80° C. A higher introduction efficiency was shown with the medium to which 10% serum was added than with the serum-free medium. A higher gene transfer activity was shown with 200 μl of the vector solution (estimated amounts: $2.8 \times 10^7$ virus particles/well) than with 100 μl of the solution (estimated amount: $1.4 \times 10^7$ virus particles/well).

BEST MODES FOR CARRYING OUT THE INVENTION (Definitions)

As used in the present specification, "gene transfer" refers to the introduction (in vivo or in vitro) of a desired natural, synthetic, or recombinant gene or gene fragment into a target cell in such a manner that the introduced gene maintains its functions. The gene or gene fragment to be introduced according to the present invention encompasses DNA, RNA, or any nucleic acid which is a synthetic analog thereof, having a specific sequence. In the present specification, the terms "gene transfer", "transfection", and "transfecting" are interchangeably used.

As used in the present specification, a "gene transfer vector", "gene vector" or "virus envelope vector" refers to a vector obtained by encapsulating an exogenous gene in a virus envelope. The virus to be used for the preparation of a gene transfer vector may be a wild-type virus or a recombinant-type virus.

In one aspect of the present invention, the virus used is a virus belonging to a family selected from the group consisting of: Retroviridae, Togaviridae, Coronaviridae, Flaviviridae, Paramyxoviridae, Orthomyxoviridae, Bunyaviridae, Rhabdoviridae, Poxyiridae, Herpesviridae, Baculoviridae, and Hepadnaviridae. In a particular aspect of the present invention, the virus used is HVJ.

As used in the present specification, "gene transfer activity" refers to the "gene transfer" activity of a vector, and can be detected by using the function of the introduced gene (e.g., in the case of an expression vector, the expression of encoded protein and/or the activity of that protein, etc.) as an index.

As used in the present specification, "inactivated" is used to refer to a virus whose genome has been inactivated. The inactivated virus is replication deficient. Preferably, the inactivation is achieved by a UV treatment or by a treatment with an alkylating agent.

As used in the present specification, an exogenous gene refers to any nucleic acid sequence contained within a gene transfer vector, where the nucleic acid sequence is not of a viral origin. In one aspect of the present invention, the exogenous gene is operably linked to an appropriate regulatory sequence to allow a gene which has been introduced via a gene transfer vector to be expressed (e.g., a promoter, an enhancer, a terminator, and a poly A addition signal which may be necessary for transcription, as well as a ribosome binding site, a start codon, a stop codon which may be necessary for translation, and the like). In another aspect of the present invention, the exogenous gene does not include any regulatory sequences for the expression of this exogenous gene. In a further aspect of the present invention, the exogenous gene is an oligonucleotide or a decoy nucleic acid.

An exogenous gene to be contained in a gene transfer vector is typically a DNA or RNA nucleic acid molecule, but the nucleic acid molecule to be introduced may include a nucleic acid analog molecule. The molecular species to be contained within the gene transfer vector may be a single gene molecular species or a plurality of different gene molecular species.

As used in the present specification, a "gene library" refers to a nucleic acid library containing a nucleic acid sequence isolated from nature or a synthetic nucleic acid sequence. Examples of sources of nucleic acid sequences isolated from nature include a genomic sequence or a cDNA sequence derived from eukaryotic cells, prokaryotic cells, or viruses, but are not limited thereto. A library obtained by adding an arbitrary sequence (e.g., a signal or tag) to a sequence isolated from nature is also encompassed by the gene library according to the present invention. In one embodiment, a gene library contains sequences such as promoters for causing transcription and/or translation of nucleic acid sequences contained therein.

In the present specification, "HVJ" and "Sendai virus" are interchangeably used.

In the present specification, "HAU" refers to a level of viral activity which can agglutinate 0.5% of chicken erythrocytes. One HAU corresponds to approximately 24,000,000 virus particles (Okada, Y. et al., Biken Journal 4, 209 to 213, 1961).

(Gene Therapy)

Therapeutic nucleic acid constructs may be administered either locally or systemically by using the gene transfer vector according to the present invention. In the case where such a nucleic acid construct includes coding sequence of a protein, the expression of the protein may be induced by the use of an endogenous mammalian promoter or a heterologous promoter. The expression of the coding sequence may be constitutive or regulated.

In the case where the gene transfer vector according to the present invention is employed as a composition for gene therapy, the administration of the vector according to the present invention may be achieved through direct injection of a vector suspension which is suspended in PBS (phosphate buffered saline), saline, etc., to local sites (e.g. intra-cancerous tissue, intrahepatic, intramuscular and intracerebral), or through intravascular administration (e.g., intraarterial, intravenous or intraportal) thereof.

In one embodiment, the gene transfer vector may be formulated generally by mixing the gene transfer vector, in a unit dosage injectable form (solution, suspension or emulsion), with a pharmaceutically acceptable carrier (i.e., one that is non-toxic to recipients at the dosages and concentrations employed and is compatible with other ingredients of the formulation). For example, the formulation preferably does not include oxidizing agents oxidizing agents and other compounds that are known to be deleterious to the gene transfer vector.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins (such as serum albumin, gelatin, or immunoglobulins); hydrophilic polymers (such as polyvinylpyrrolidone); amino acids (such as glycine, glutamic acid, aspartic acid, or arginine; monosaccharides, disaccharides, and other carbohydrates (including cellulose or its derivatives, glucose, mannose, or dextrins); chelating agents (such as EDTA); sugar alcohols (such as mannitol or sorbitol); counterions (such as sodium); and/or nonionic detergents (such as polysorbates or poloxamers), or PEG.

A pharmaceutical composition containing a gene transfer vector may typically be stored as an aqueous solution in a unit- or multi-dosage container, e.g., sealed ampule or vial.

The present invention also provides a pharmaceutical package or kit including one or more containers filled with one or more ingredients of the pharmaceutical composition according to the present invention. Furthermore, the polypeptide according to the present invention may be used along with other therapeutic compounds.

A pharmaceutical composition containing the gene transfer vector according to the present invention will be formulated and dosed in a fashion consistent with good medical practice, taking into account the clinical condition of the individual patient (e.g., condition to be prevented or treated), the site of delivery of the composition containing the gene transfer vector, the target tissue, the administration method, the scheduling of administration, and other factors known to those skilled in the art. Accordingly, an "effective amount" or an appropriate dosage of the gene transfer vector described in the present specification is determined by such considerations.

For example, in the case where the gene vector according to the present invention is administered to a mouse, the equivalent of 20 to 20,000 HAU, preferably 60 to 6,000 HAU, and more preferably 200 to 2,000 HAU of gene vector is to be administered per mouse. The amount of exogenous gene contained in the administered gene vector is 0.1 to 100 µg, preferably 0.3 to 30 µg, and more preferably 1 to 10 µg per mouse.

In the case where the gene vector according to the present invention is administered to a human, the equivalent of 400 to 400,000 HAU, preferably 1,200 to 120,000 HAU, and more preferably 4,000 to 40,000 HAU of gene vector is to be administered per subject. The amount of exogenous gene contained in the administered gene vector is 2 to 2,000 µg, preferably 6 to 600 µg, and more preferably 20 to 200 µg per subject.

It is intended that the following examples are illustrative and not limitative of the present invention.

EXAMPLES

1. A Gene Transfer Vector Preparation Employing Freezing and Thawing, and its Use Example 1

Preparation of an HVJ Envelope Vector by Freezing and Thawing

The luciferase gene was used as an exogenous gene. After freezing and thawing a recombinant HVJ virus various times, the gene was introduced into cultured cells.

To 500 µl of TE, 750 µg of luciferase expression vector pcOriPLuc (Saeki and Kaneda et al., Human Gene Therapy, 11, 471 to 479(2000)) and various concentrations of HVJ virus were mixed. The HVJ virus concentration was adjusted to 10, 25, 50, or 100 HAU/µl. This solution was divided into twelve aliquots, each of which was stored at 4° C., and frozen with dry ice and thereafter thawed, this was repeated up to thirty times. A solution which had experienced a predetermined number of times of freezing and thawing was added to a medium for BHK-21 cells (24 well-dish, $4 \times 10^4$ cells/dish, 0.5 ml DMEM, 10% FCS). After the cells were allowed to react with 5% $CO_2$ at 37° C. for 20 minutes, the cells were washed with PBS, and another 0.5 ml of the culture solution was added and cultured for 24 hours.

The medium was removed. After 500 µl of 1× cell Culture Lysis Reagent (Promega) was added to the cells to dissolve the cells, the solution was placed in a microtube and centrifuged. From 20 µl of the resultant supernatant, the luciferase activity was measured by using Promega Luciferase Assay System and Lumat LB9501 Luminophotometer. The measurements were taken three times for each solution, and a mean value was obtained.

The results are shown in FIG. 1. The luciferase activity increased as the number of times of freezing and thawing for recombinant HVJ virus increased. With twenty times of freezing and thawing, tenfold or more luciferase expression was observed as compared to that observed with three times of freezing and thawing. From these results, it was confirmed that, under the conditions used in this example, the number of times of freezing and thawing for the recombinant HVJ virus is preferably five or more, and more preferably about 15 to about 20.

Example 2

Gene Transfer Efficiency of HVJ Envelope Vector which was Prepared by Freezing and Thawing After freezing and thawing a recombinant HVJ virus similar to that used in Example 1 thirty times, gene transfer efficiency into the cell was examined while ensuring that the same number of viruses were added to the host cell.

The results are shown in FIG. 2. In FIG. 2, at 500 HAU on the X axis, for example, the solution having a virus concentration of 10 HAU/µl was added in an amount of 50 µl, as opposed to 5 µl for the 100 HAU/µl solution. As shown in FIG. 2, the gene expression efficiency of the solution having a virus concentration of 100 HAU/µl decreased by about 50% as compared to that associated with a concentration of 10 to 50 HAU/µl. From these results, it was confirmed that, under the conditions in this example, the recombinant virus concentration was preferably in a range of 10 to 50 HAU/µl.

Moreover, after freezing and thawing a recombinant HVJ virus twenty-nine times, freezing was performed for a thirtieth time, and the HVJ virus solution was stored in this frozen state for a week, and thereafter thawed to be added to the cells. As a result, the recombinant HVJ virus which was stored in a frozen state for one week also exhibited the same level of luciferase gene expression as that of the virus which experienced thirty consecutive times of freezing and thawing.

Example 3

Measurement of Gene Transfer Efficiency Using a Luciferase Expression Vector

An HVJ envelope vector was prepared by employing various amounts of luciferase expression vector, and the gene transfer efficiency into a host cell was examined.

The amount of HVJ virus was 50 HAU per µl of TE. The amount of luciferase expression vector pcOriPLuc was 0.05, 0.1, 0.25, 0.5, 1.0, 1.5, 2.0, 3.0, or 5.5 µg per µl of TE. Twenty times of freezing and thawing were carried out, and the final volume of the solution was adjusted to 100 µl, and thereafter luciferase activity was measured by the same method as that of Example 1.

The results are shown in FIG. 3. the expression amount increased in a dose-dependent manner until the added amount of expression vector pcOriPLuc (about 9.5 kb) as an exogenous gene reached 1.5 µg; thereafter, there was hardly any change in the expression amount. From the above results, it was confirmed that, under the conditions employed in this example, it is preferable to use 1.5 µg/µl or more of exogenous gene DNA for gene transfer.

Example 4

Effects of Types of Buffers on the Gene Transfer Efficiency

The gene transfer efficiency into the host cell was examined while varying the types of buffers used for the preparation of an HVJ envelope vector.

The amount of HVJ virus was 50 HAU per µl of buffer, the amount of luciferase expression vector pcOriPLuc was 15 µg/µl. As the buffer, TE, PBS, or BSS (137 mM NaCl, 5.4 mM KCl, 10 mM Tris-HCl, pH 7.5), or those obtained by adding sucrose to these buffers at a final concentration of 0 mM, 20 mM, 40 mM, or 60 mM were used. Twenty times of freezing and thawing were carried out, and the final volume of the solution was adjusted to 100 µl, and thereafter luciferase activity was measured by the same method as that of Example 1.

Figure 4:
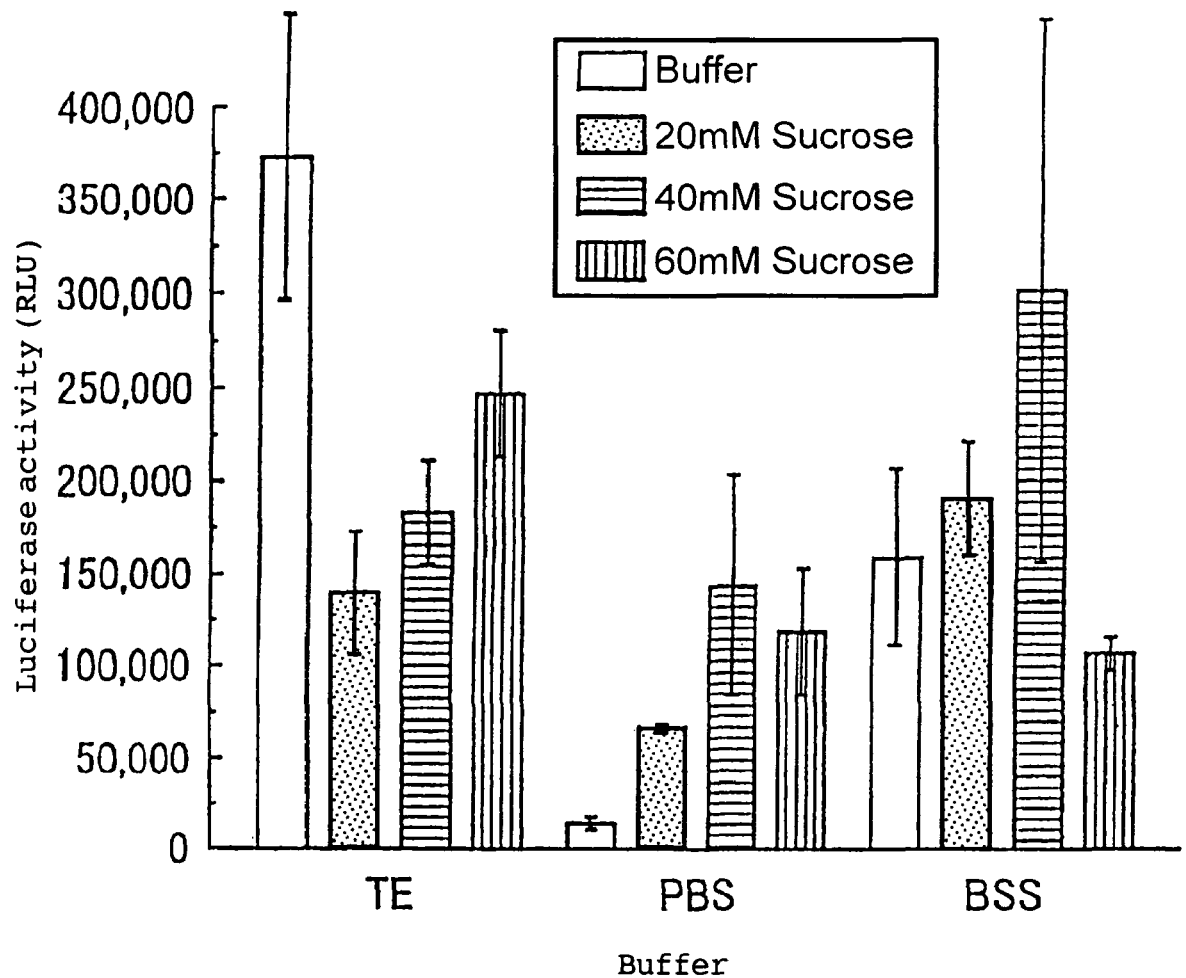
FIG. 4 shows results of luciferase activity measurement in the case where various types of buffers were employed for the preparation of HVJ envelope vectors.

The results are shown in FIG. 4. It was confirmed that, under the conditions employed in this example, it is preferable to use TE alone as the buffer for the preparation of a recombinant HVJ virus.

Example 5

Comparison Between an AVE (Artificial Viral Envelope) Type Vector and the HVJ Envelope Vector According to the Present Invention A gene transfer employing inactivated HVJ-liposome (of the AVE type having the most excellent gene transfer efficiency (Saeki, Y et al., Human Gene Therapy, 8, 2133 to 2141(1997)), which is a conventional gene transfer vector, and the method according to the present invention were compared.

The amount of HVJ-liposome or HVJ virus was 50 HAU per µl of TE, and the amount of luciferase expression vector pcOriPLuc was 1.5 µg/µl. The number of times of freezing and thawing for the recombinant HVJ virus was twice or fifteen times. The other conditions were the same as in Example 1, except that human embryonic kidney cell line HEK293 was used as host cells.

Figure 5:
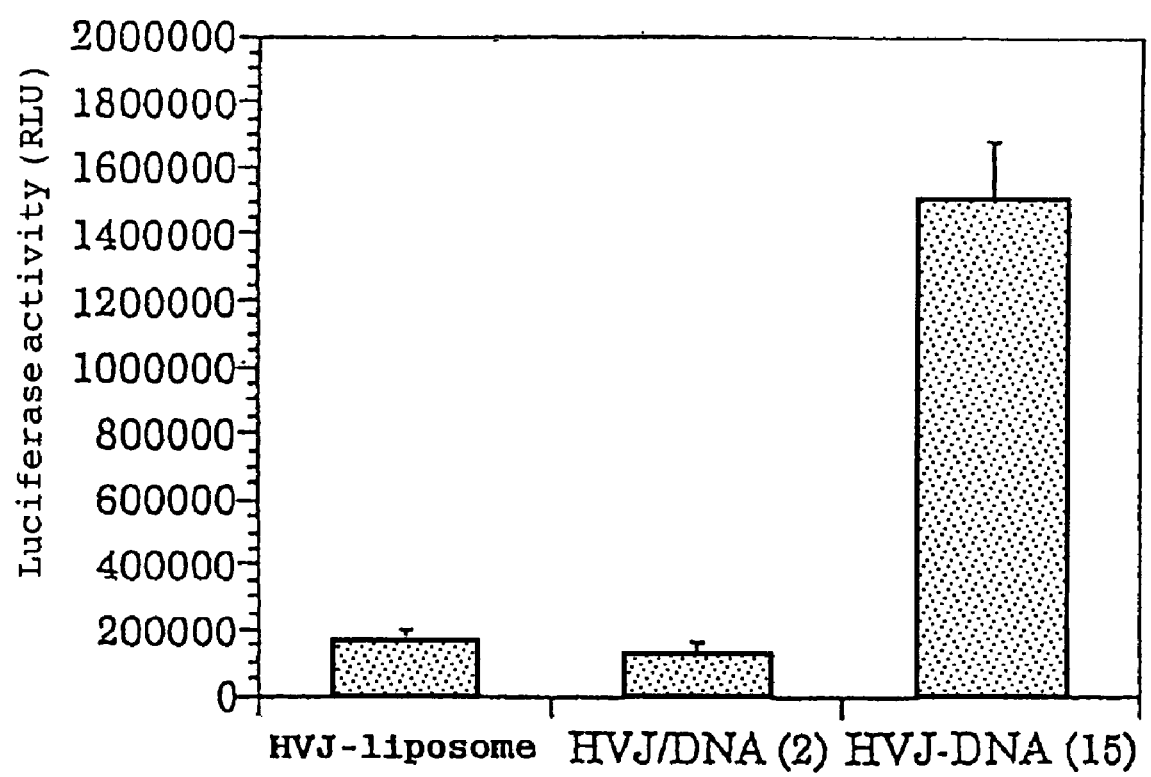
FIG. 5 shows results of comparison between the gene transfer employing a conventional gene transfer vector, inactivated HVJ-liposome and the method according to the present invention.

The results are shown in FIG. 5. It was confirmed that the method according to the present invention which repeats fifteen times of freezing and thawing of the HVJ envelope vector is far more excellent in gene transfer efficiency than the conventional method employing HVJ-liposome.

Example 6

Introduction Efficiency of a Synthetic Oligonucleotide

A synthetic oligonucleotide (20 bp) fluorescence-labeled with FITC (fluorescein isothiocyanate), at a concentration of 1 mg/ml, was mixed with inactivated HVJ virus. After this solution was frozen and thawed twenty times, the solution was allowed to react with BHK-21 cells for 20 minutes. The fluorescence signal was observed 17 hours later. As a result, fluorescence accumulation was observed in the nuclei of almost 100% of the cells. From these results, it was confirmed that the method according to the present invention is also effective for introducing a synthetic nucleic acid into cells.

Example 7

Introduction Efficiency of the GFP Gene

After a mixed solution of GFP (green fluorescence protein) gene and inactivated HVJ virus was frozen and thawed twenty times. 2 ng-5 µl of the mixed solution was Injected into a rat cerebrum. As a result, a fluorescence signal was observed at the injection site. Moreover, an HVJ envelope vector utilizing the GFP gene was frozen and stored for 3 months, and thereafter injected into a rat cerebrum. Similarly, a fluorescence signal due to the expression of the GFP gene was observed at the injection site.

From the above results, it was confirmed that the method according to the present invention is certainly capable of realizing gene transfer in vivo as well. Moreover, it was also confirmed that frozen storage of an HVJ envelope vector is possible.

2. Preparation of Gene Transfer Vector Utilizing a Detergent, and its Use

Example 8

Preparation of an Inactivated HVJ Envelope Vector Utilizing a Detergent

Figure 6:
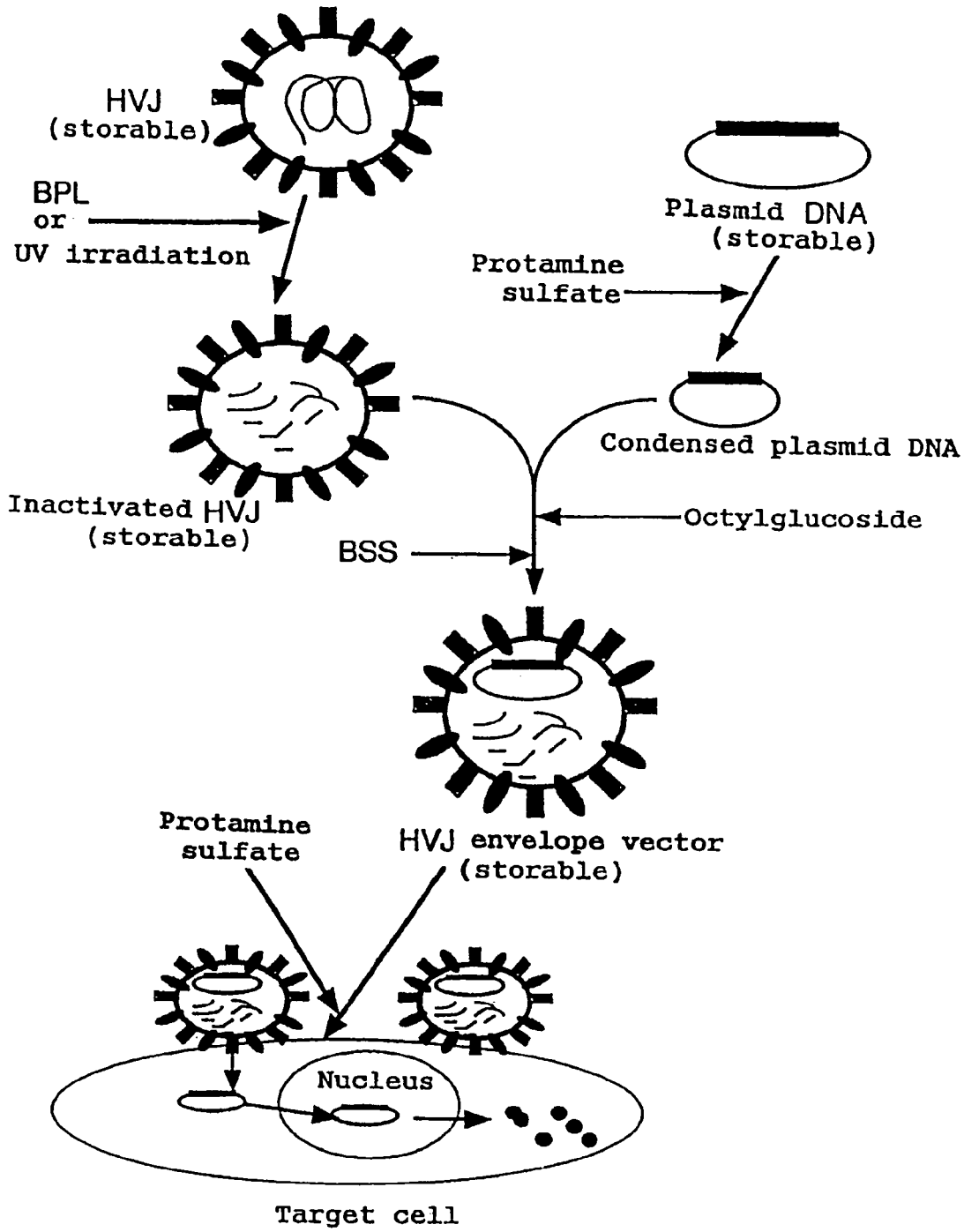
FIG. 6 schematically illustrates a preparation method for an inactivated HVJ envelope vector where a detergent was employed.

A preparation method for an inactivated HVJ envelope vector utilizing a detergent is schematically shown In FIG. 6.

(1: Growth of HVJ)

In general, HVJ grown by inoculating a fertilized chicken egg with the seed virus may be used. However, HVJ grown by utilizing cultured cells (e.g., simian or human) or a persistent infection system (i.e., a culture solution to which a hydrolase such as trypsin is added to cultured tissue), or HVJ grown by infecting cultured cells with cloned virus genome to cause persistent infection are applicable.

In the present example, the growth of HVJ was carried out as follows.

HVJ seed virus was grown by utilizing a SPF (Specific Pathogen Free) fertilized egg. The isolated and purified HVJ (Z species) was dispensed into a tube for storing cells, and stored in liquid nitrogen with 10% DMSO added thereto. Thus, HVJ was prepared.

Chicken eggs immediately after fertilization were obtained, and placed in an incubator (SHOWA-FURANKI P-03 type, capable of accommodating about 300 chicken eggs), and bred for 10 to 14 days under the conditions of 36.5° C. and 40% or more humidity. In a darkroom, the viability of the embryo as well as an air chamber and a chorioallantois were confirmed by using an egg tester (one in which light from a light bulb is led through a window having a diameter of about 1.5 cm). A virus-injected site was marked in pencil about 5 mm above the chorioallantois (the position was selected so as avoid any thick blood vessels). The seed virus (which was taken out of the liquid nitrogen) was diluted by 500 times with a polypeptone solution (to which 1% polypeptone, 0.2% NaCl was mixed, and which was prepared so as to have pH 7.2 with 1 M NaOH, then autoclave-sterilized, and stored at 4° C.), and left at 4° C. The egg was disinfected with Isodine™ and alcohol. A small hole was made in the virus-injected site with a pick. Using a needled 1 ml syringe (26 gauge), 0.1 ml of the diluted seed virus was injected so as to be in the chorioallantoic cavity. Molten paraffin (melting point: 50 to 52° C.) was placed on the hole using a Pasteur pipette to close the hole. The egg was placed in an incubator and bred for three days under the conditions of 36.5° C. and 40% or more humidity. Then, the inoculated egg was left overnight at 4° C. On the following day, the air chamber portion of the egg was broken with a pincette, and a 10 ml syringe with an 18 gauge needle was placed in the chorioallantois so as to suck the chorioallantoic fluid, which was collected in a sterilized bottle and stored at 4° C.

(2: Purification of HVJ)

HVJ may be purified by a purification method utilizing centrifugation, a purification method utilizing a column, or any other purification methods known in the art.

(2.1: Purification Method Through Centrifugation)

In short, a solution containing grown viruses was collected, and the solution was centrifuged with low speed to remove the tissue or cell debris in the culture solution and the chorioallantoic fluid. A supernatant thereof was purified through high-speed centrifugation (27,500×g, 30 minutes) and ultracentrifugation (62,800×g, 90 minutes) utilizing a sucrose density gradient (30 to 60% w/v). Care should be taken to treat the virus as gently as possible during purification, and to store the virus at 4° C.

Specifically, in the present example, HVJ was purified by the following method.

About 100 ml of HVJ-containing chorioallantoic fluid (the chorioallantoic fluid from a chicken egg containing HVJ, which was collected and stored at 4° C.) was placed in two 50 ml centrifuge tubes with a wide-mouth Komagome type pipette (see Saeki, Y., and Kaneda, Y: Protein modified liposomes (HVJ-liposomes) for the delivery of genes, oligonucleotides and proteins. Cell Biology; A laboratory handbook (2nd edition) ed. by J. E. Celis (Academic Press Inc., San Diego) vol. 4, 127 to 135, 1998), centrifuged with a low-speed centrifuge at 3000 rpm and at 4° C. for 10 minutes (the brakes were turned off). Thus, the tissue debris from the egg was removed.

After the centrifugation, the supernatant was dispensed in four 35 ml centrifuge tubes (designed for high-speed centrifugation), and centrifuged for 30 minutes with an angle rotor at 27,000 g, (the accelerator and the brakes were turned on). The supernatant was removed, BSS (10 mM Tris-HCl (pH 7.5), 137 mM NaCl, 5.4 mM KCl; autoclaved and stored at 4° C.) (the BSS is replaceable by PBS) was added to the precipitate in an amount of about 5 ml per tube, and allowed to stand still at 4° C. overnight. While gently pipetting with a wide-mouth Komagome type pipette, the precipitate was disentangled and collected in one tube, and was similarly centrifuged for 30 minutes with an angle rotor at 27,000 g. The supernatant was removed, and about 10 ml of BSS was added to the precipitate, and the precipitate was allowed to stand still at 4° C. overnight. While gently pipetting with a wide-mouth Komagome type pipette, the precipitate was disentangled, and centrifuged for 10 minutes with a low-speed centrifuge at 3000 rpm and at 4° C. (the brakes were turned off), thereby removing the tissue debris and agglutination masses of virus which had not been completely removed. The supernatant was placed in a fresh sterilized tube, and stored at 4° C. as the purified virus.

To 0.1 ml of this virus solution, 0.9 ml of BSS was added, and the absorption at 540 nm was measured with a spectrophotometer. The virus titer was converted into an erythrocyte agglutination activity (HAU). An absorption value 1 at 540 nm approximately corresponded to 15,000 HAU. It is considered that HAU is substantially in proportion with the fusion activity. Alternatively, the erythrocyte agglutination activity may be measured by actually using a solution containing chicken erythrocytes (0.5%), (see DOUBUTSU SAIBO RIYO JITSUYOKA MANUAL (or "Practice Manual for Using Animal Cells"), REALIZE INC. (ed. by Uchida, Oishi, Furusawa) pp. 259 to 268, 1984).

Furthermore, a purification of HVJ using a sucrose density gradient may be performed as necessary. Specifically, a virus suspension is placed on a centrifuge tube in which 60% and 30% sucrose solutions (autoclave-sterilized) were layered, and a density gradient centrifugation is performed for 120 minutes at 62,800×g. After the centrifugation, a band which is observed on the 60% sucrose solution layer is recovered. The recovered virus suspension is dialyzed overnight at 4° C. against an external solution of BSS or PBS, thereby removing the sucrose. In the case where the virus suspension is not to be immediately used, glycerol (autoclave-sterilized) and a 0.5 M EDTA solution (autoclave-sterilized) are added to the virus suspension so as to attain final concentrations of 10% and 2 to 10 mM, respectively, and gently frozen at −80° C., and finally stored in liquid nitrogen (the frozen storage can be achieved with 10 mM DMSO, instead of glycerol and a 0.5 M EDTA solution).

(2.2: Purification Method Utilizing Columns and Ultrafiltration)

Instead of the purification method through centrifugation, purification of HVJ utilizing columns is also applicable to the present invention.

Briefly, concentration (about 10 times) via ultrafiltration utilizing a filter having a molecular weight cut-off of 50,000 and elution via ion exchange chromatography (0.3 M to 1 M NaCl) were performed to achieve purification.

Specifically, in the present example, the following method was used to purify HVJ by columns.

After a chorioallantoic fluid was collected, the chorioallantoic fluid was filtrated through a membrane filter (80 μm to 10 μm). To the chorioallantoic fluid, 0.006 to 0.008% BPL (final concentration) was added (4° C., 1 hour), so as to inactivate HVJ. The chorioallantoic fluid was incubated for 2 hours at 37° C., thereby inactivating BPL.

By a tangential flow ultrafiltration method using 500KMWCO (A/G Technology, Needham, Mass.), about 10 times concentration was achieved. As a buffer, 50 mM NaCl, 1 mM $MgCl_2$, 2% mannitol, and 20 mM Tris (pH 7.5) were used. An HAU assay indicated an HVJ yield of approximately 100%. Thus, excellent results were obtained.

By a column chromatography method (buffer: 20 mM Tris HCl (pH 7.5), 0.2 to 1 M NaCl) using Q Sepharose FF (Amersham Pharmacia Biotech KK, Tokyo), HVJ was purified. The yield was 40 to 50%, and the purity was 99% or more.

A HVJ fraction was concentrated by a tangential flow ultrafiltration method using 500KMWCO (A/G Technology).

(3: Inactivation of HVJ)

In the case where It was necessary to Inactivate HVJ, this was performed through UV light irradiation or an alkylating agent treatment as described below.

(3.1: UV Light Irradiation Method)

One milliliter of HVJ suspension was placed in a dish having a diameter of 30 mm, and subjected to an irradiation at 99 or 198 $mJ/cm^2$. Although gamma-ray irradiation is also applicable (5 to 20 Gy), it does not provide complete inactivation.

(3.2: Treatment Using an Alkylating Agent)

Immediately before use, 0.01% β-propiolactone was prepared in 10 mM $KH_2PO$. The solution was kept at a low temperature during preparation, and the operation was quickly performed.

To the HVJ suspension obtained immediately after purification, β-propiolactone was added so as to finally become 0.01%, and incubated on ice for 60 minutes. Thereafter, the mixture was incubated at 37° C. for 2 hours. The mixture was dispensed into Eppendorf tubes in an amount of 10,000 HAU per tube, and centrifuged for 15 minutes at 15,000 rpm. The precipitate was stored at −20%. Instead of using the aforementioned inactivation method, without storing the precipitate at −20° C. DNA may be allowed to be incorporated through a detergent treatment to construct a vector.

(4: Construction of an HVJ Envelope Vector)

To the HVJ which had been stored, 92 µl of a solution containing 200 to 800 µg of exogenous DNA was added, and allowed to be well suspended through pipetting This solution can be stored at −20° C. for at least 3 months. By adding protamine sulfate to the DNA before mixing with HVJ, the expression efficiency was enhanced twofold or more.

This mixture was placed on ice for 1 minute, and 8 µl of octylglucoside (10%) was added. The tube was shaken on ice for 15 seconds, and allowed to stand still on ice for 45 seconds. The treatment time with the detergent is preferably 1 to 5 minutes. Instead of octylglucoside, detergents such as Triton-X100 (t-octylphenoxypolyethoxyethanol), CHAPS(3-[(3-cholamidopropyl)-dimethylammonio]-1-propane sulfonate), or NP-40(nonylphenoxy polyethoxy ethanol) may also be used. The final concentrations of Triton-X100, NP-40, and CHAPS are preferably 0.24 to 0.80%, 0.04 to 0.12%, and 1.2 to 2.0%, respectively.

One milliliter of cold BSS was added, and the solution was immediately centrifuged for 15 minutes at 15,000 rpm. To the resultant precipitate, 300 µl of PBS or saline, etc., was added, and allowed to be suspended through vortex or pipetting. The suspension may be directly used for gene transfer or may be used for gene transfer after storage at −20° C. After being stored for at least 2 months, this HVJ envelope vector maintained the same level of gene transfer efficiency.

Example 9

Ratio Between F1 Protein and HN Protein in the HVJ Envelope Vector (1: Sample Preparation)
(i) An amount of purified HVJ equivalent to 10,000 HAU was centrifuged for 15 minutes at 15,000 rpm, and the precipitate was suspended in 300 µl of PBS, and stored at −20%.
(ii) An amount of purified HVJ equivalent to 10,000 HAU was subjected to UV light irradiation (198 mJ/cm$^2$), and thereafter centrifuged for 15 minutes at 15,000 rpm, and the precipitate was suspended in 300 µl of PBS, and stored at −20° C.
(iii) An amount of purified HVJ equivalent to 10,000 HAU was subjected to UV light irradiation (198 mJ/cm$^2$), and thereafter centrifuged for 15 minutes at 15,000 rpm. To the precipitate, 200 µg of pcLuci DNA (solution 92 µl) was added, and allowed to be suspended through pipetting. The suspension was placed on ice, and 8 µl of octylglucoside (10%) was added. The tube was shaken for 15 seconds by hand, and settled on ice for 45 seconds. One milliliter of cold BSS was added, and immediately centrifuged for 15 minutes at 15,000 rpm. Thereafter, the precipitate was allowed to be suspended in 300 µl of PBS, and stored at −20° C.

(2: Protein Electrophoresis)
A×5 Laemli sample buffer was added to the three kinds of samples (5, 10, 20 µl), and a 10% SDS-polyacrylamide gel electrophoresis was performed. After electrophoresis, the gel was stained with Coomassie Blue. After destaining, the gel was affixed on cellophane paper and dried.

Figure 7:
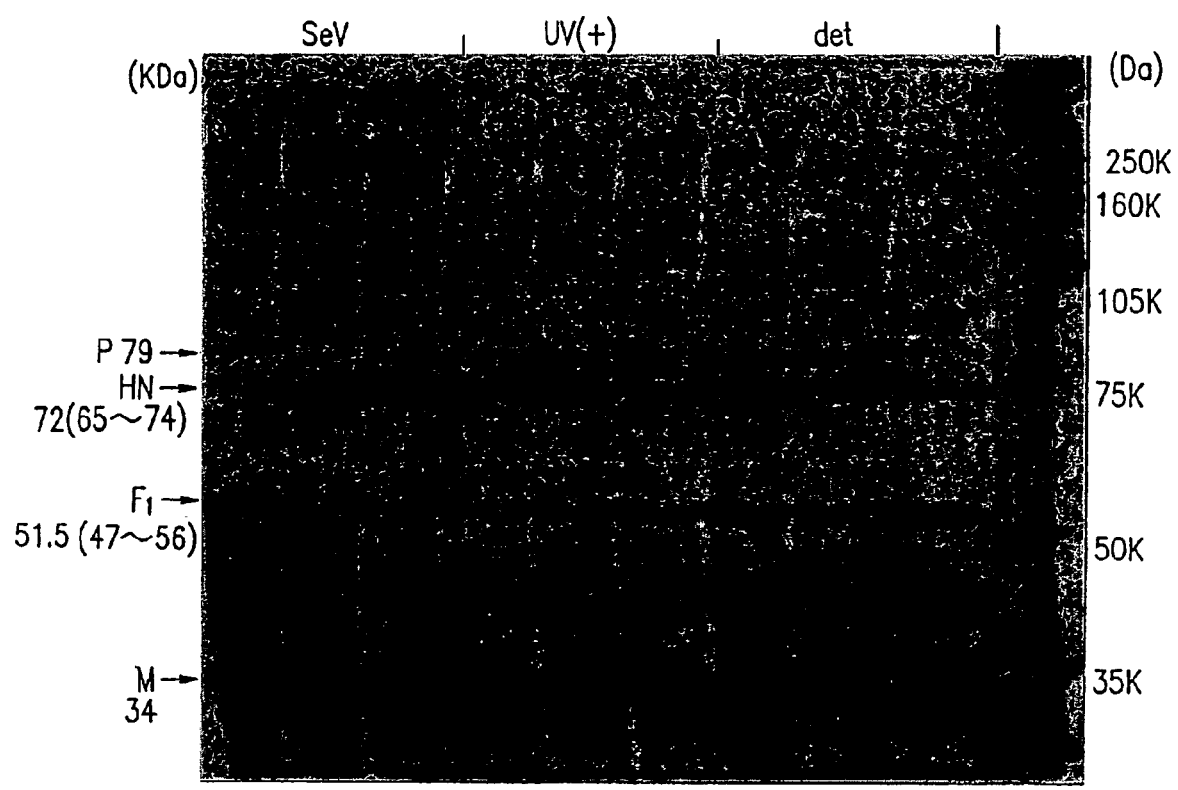
FIG. 7 is a diagram illustrating an SDS-PAGE pattern of proteins contained in an HVJ envelope vector which was prepared using a detergent.

(3: Protein Identification)
The samples which had been subjected to electrophoresis and staining were inserted into LAS2000 (Fuji Film, Tokyo) (FIG. 7), the concentration of protein bands corresponding to F1 and HN were measured. Per each type of sample, three different amounts were subjected to electrophoresis. The F1/HN density of each was calculated, and a mean and a standard deviation were calculated for each sample.

(4: Results)
F1/HN was consistently about 1.7 for samples (i), (ii), and (iii). Considering the molecular weights of F1 (51 kD) and HN (68 kDa), the molar ratio would be about 2.3. This is also consistent with the report (Exp. Cell Res. 142, 95 to 101, 1985) that the optimum fusion for reconstituted liposome using F1 and H can be achieved by a F1/HN value of about 2. In the reconstituted types reported by other researchers, this ratio is different from that of the wild-type virus (J. Virol. 67, 3312 to 3318, 1993). The other protein compositions were also substantially the same between HVJ and the HVJ envelope vector.

Example 10

DNA Encapsulation into the HVJ Envelope Vector and Encapsulation Rate (1: Electron Microscopic Images of HVJ Envelope Vector (with DNA Encapsulated or Unencapsulated))
As described above, 130 µg of pSFV-LacZ (14.5 kb) was encapsulated in HVJ (UV light inactivated) of 10,000 HAU, and an HVJ envelope vector was prepared.

The HVJ envelope vector after encapsulation was suspended in 300 µl of PBS, and stored at −20° C. Ten days later, 1 µl of the suspension was placed on a grid, and observed via electron microscopy by negative staining. As a control, an HVJ envelope vector was used in which DNA was not encapsulated.

Figure 8A:
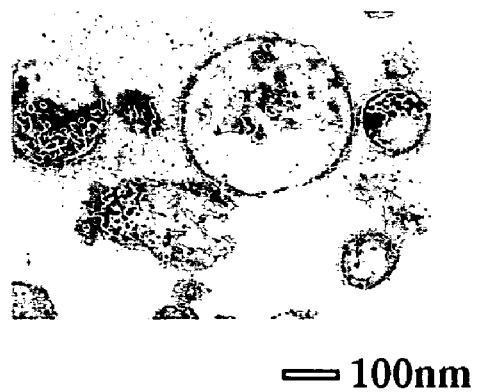
FIGS. 8A-8C are electron micrographs of an HVJ envelop vector using negative staining, showing (1) untreated HVJ (FIG. 8A); (2) HVJ containing no DNA, which was subjected to an octylglucoside treatment (FIG. 8B); and (3) HVJ containing DNA, which was subjected to an octylglucoside (FIG. 8C).
Figure 8B:
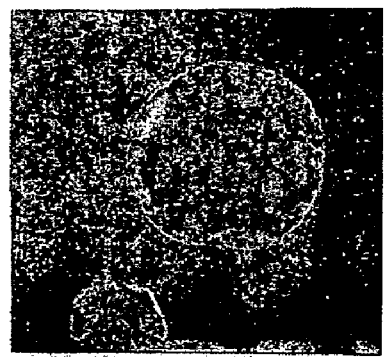
Figure 8C:
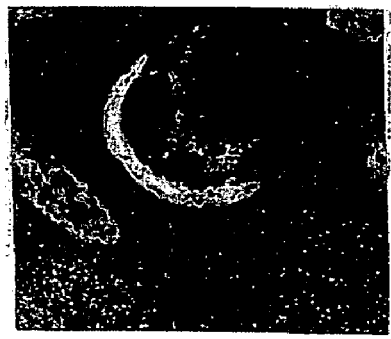

(Results)
The results are shown in FIGS. 8A-8C. A majority of the HVJ envelope vectors had substantially the same outer configuration as that of the HVJ virus observed in the past itself. As compared with the HVJ envelope vector in which DNA was not encapsulated, a structure having a high electron density was observed in the HVJ envelope vector in which DNA was employed. On the other hand, the unencapsulated HVJ envelop vectors had a high internal transmittance, and it was inferred that the virus genome had been destroyed or lost.

(2: DNA Encapsulation Rate into HVJ Envelope Vector)
pcLuci (7.4 kb) 15.7 µg was encapsulated in HVJ (UV light inactivated) of 6,700 HAU in the aforementioned manner, thereby preparing an HVJ envelope vector. The HVJ envelope vector was suspended in 300 µl of BSS, and treated with 15 units of Micrococcal nuclease, 2 mM CaCl$_2$, and 20 µg/ml of RNaseA at 20° C. for 30 minutes, and dialyzed against one liter of PBS (4° C., overnight). The HVJ envelope vector was treated with 1% SDS for 1 minute at 37° C. The HVJ envelope vector was treated with 500 µl of phenol and 500 µl of chloroform-isoamyl alcohol, and thereafter, subjected to ethanol precipitation. The precipitate was suspended in 100 µl of BSS, and measurements at 260 nm or 280 nm were taken with a spectrophotometer.

(Results)
The yield Was 85.7%. By conversion from this, the DNA incorporation efficiency into the HVJ envelope vector was 3.8%. The incorporation efficiency in the case where 279 µg of pcLuci was allowed to be incorporated in HVJ of 10,000 HAU was 7.2%.

From the above, the DNA incorporation efficiency into HVJ of 10,000 HAU is inferred to be about 6 to 7% in the case where octylglucoside is used, but may somewhat vary depending on the amount of DNA used. Moreover, it has been found that the introduction efficiency increases when protamine sulfate is present with the DNA and HVJ envelope vector, this is considered to be because the DNA encapsulation efficiency into the HVJ envelope vector was increased. It is inferred that, with Triton-X100 or NP-40, the efficiency is further increased to about 10 to 40%.

Example 11

Gene Transfer to Cells Via an HVJ Envelope Vector (1: Gene Transfer Method)

An amount equivalent to 1,000 HAU was placed into an Eppendorf tube (30 μl), and 5 μl of protamine sulfate (1 mg/ml) was added. The medium for BHK-21 cells (which were sown in 6 wells in an amount of 200,000 cells per well on the previous day) was exchanged, and 0.5 ml of medium (10% FCS-DMEM) was added per well. To each well, a mixture of the aforementioned vector (equivalent to 1,000 HAU) and protamine sulfate was added, and the plate was shaken back and forth and from right to left, whereby the vector and cells were well mixed. The mixture was left in a 5% $CO_2$ incubator for 10 minutes at 37° C.

The medium was exchanged, and left overnight (16 hrs to 24 hrs) at 37° C. in a 5% $CO_2$ incubator, after which the gene expression was examined. As for luciferase (pcLuci: a luciferase gene having a CMV promoter), the cells were lysed with 0.5 ml of Cell Lysis Buffer (Promega), and the activity in 20 μl of the solution was measured by using a luciferase assay kit (Promega). As for green fluorescence protein (pCMV-GFPE; Promega), the cells were observed under fluorescence microscopy in their intact form, and 5 to 8 fields were observed at a magnification rate of 400, and the ratio of cells which generated fluorescence was calculated.

(2: Study of Conditions Imposed on the Introduction Efficiency for Cultured Cells)

BHK-21 cells were used as cultured cells.

(2.1 Study of Octylglucoside (OG) Concentration in the Preparation of HVJ Envelope Vector)

The following modifications were made to the gene transfer method of (1) above, and the effects of octylglucoside (OG) on the gene transfer via the HVJ envelope vector at the following concentrations (i.e., the final concentrations of OG used for the preparation of the HVJ envelope vector) were examined:

(A) octylglucoside concentration: 1, 2, or 3%;

The duration for which the inactivated HVJ was treated with OG at the time of preparing the HVJ envelope vector: 1 minute, 5 minutes, or 10 minutes;

An ultrasonic treatment was performed (sonic) or not performed.

(B) octylglucoside concentration: 0.125 to 1.25%;

The volume of the vector used for transfection: 10 μl, 100 μl.

(C) octylglucoside: 0.55 to 0.8%:

Transfection time: 30 minutes, overnight (O/N).

Figure 9A:
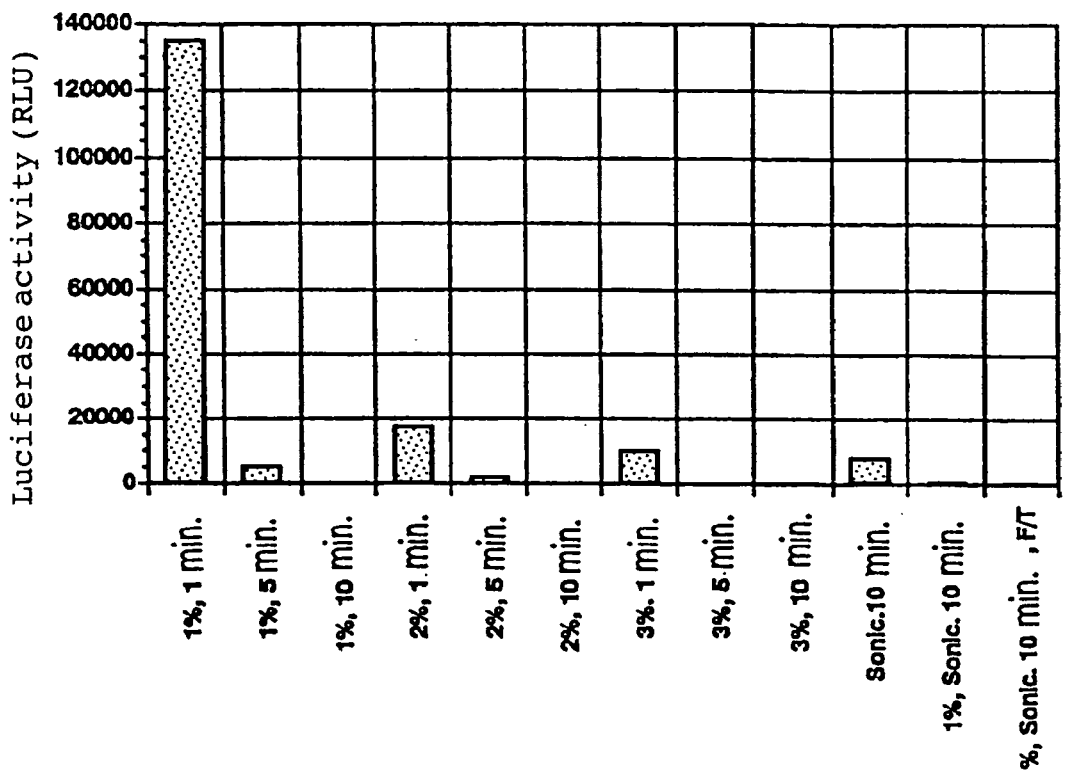
FIGS. 9A to 9C are graphs representing gene transfer efficiency represented in terms of luciferase activity levels which were taken at the respective octylglucoside concentrations; the respective treatment times for HVJ with octylglucoside; whether an ultrasonic treatment was conducted (sonic) or not; and the respective vector volumes used, as shown in the figures.
Figure 9B:
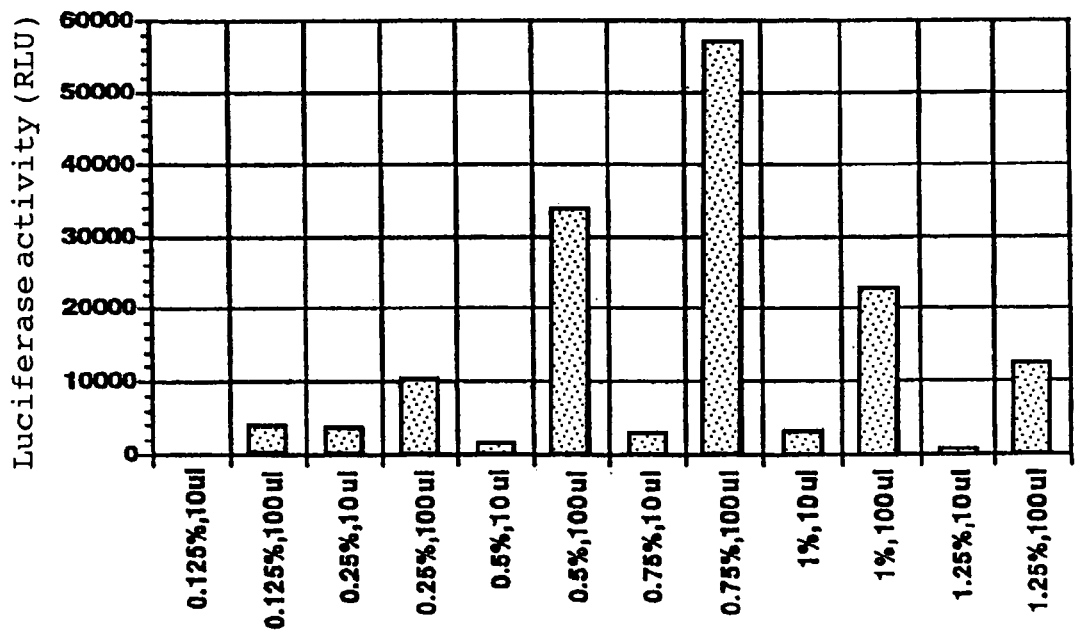
Figure 9C:
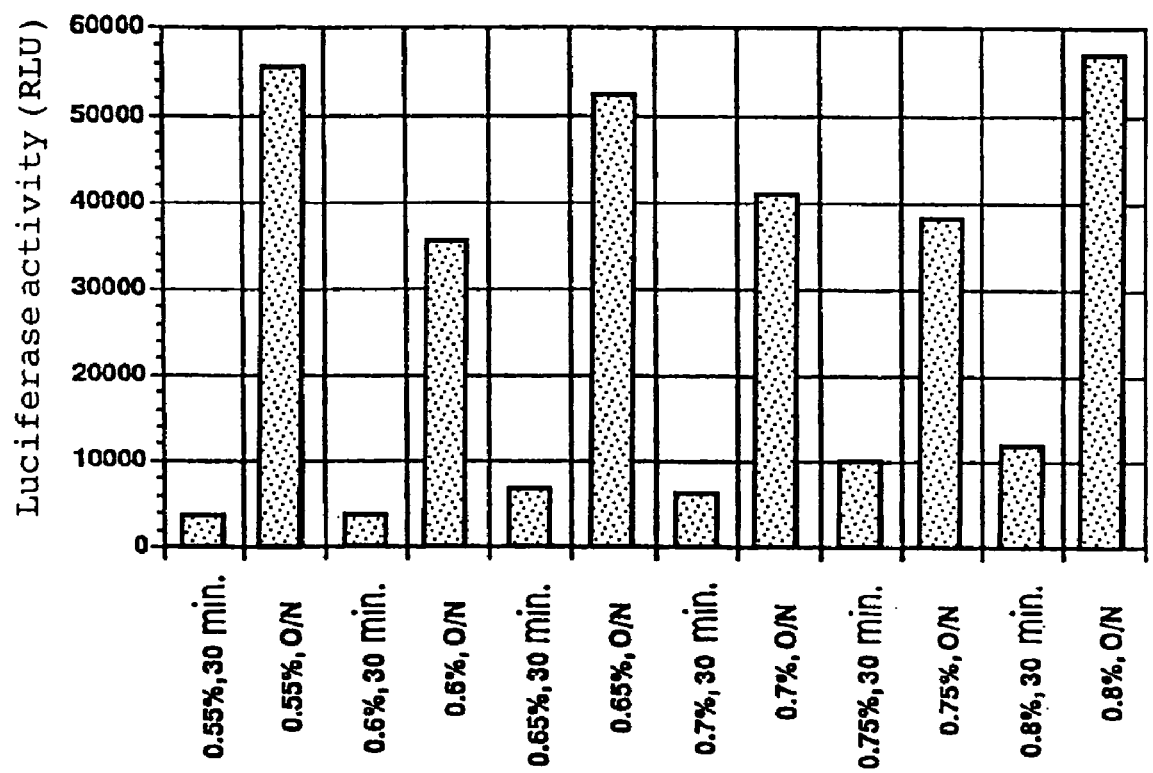
Figures 1, 10A:
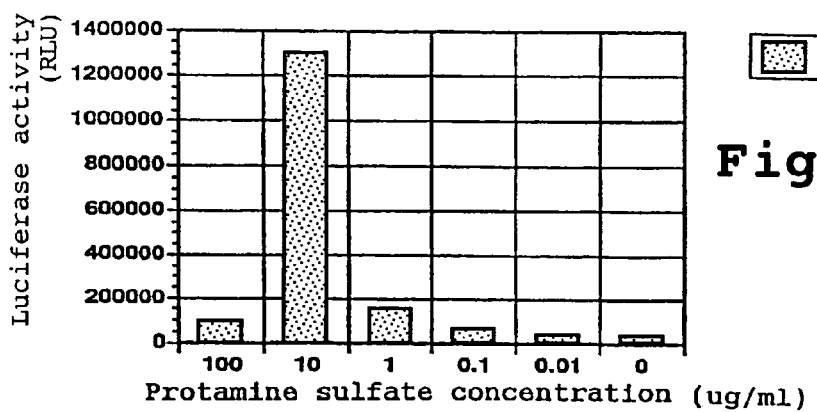
Figures 2, 10A:
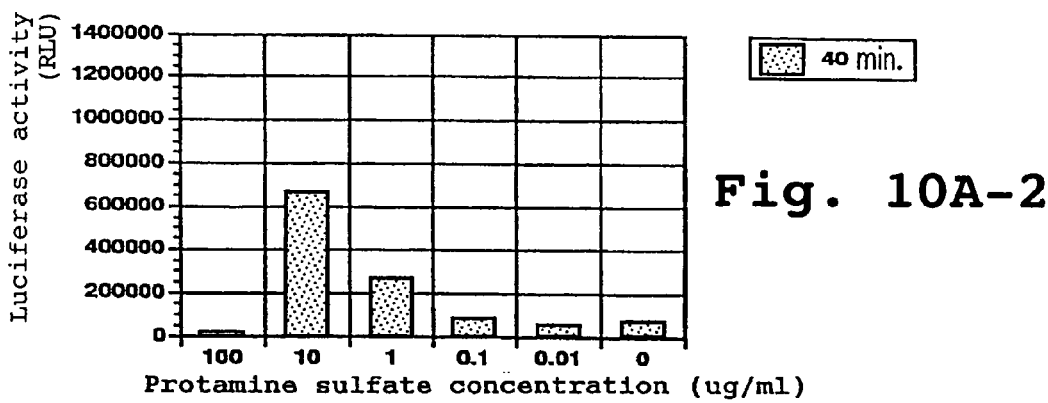
Figures 3, 10A:
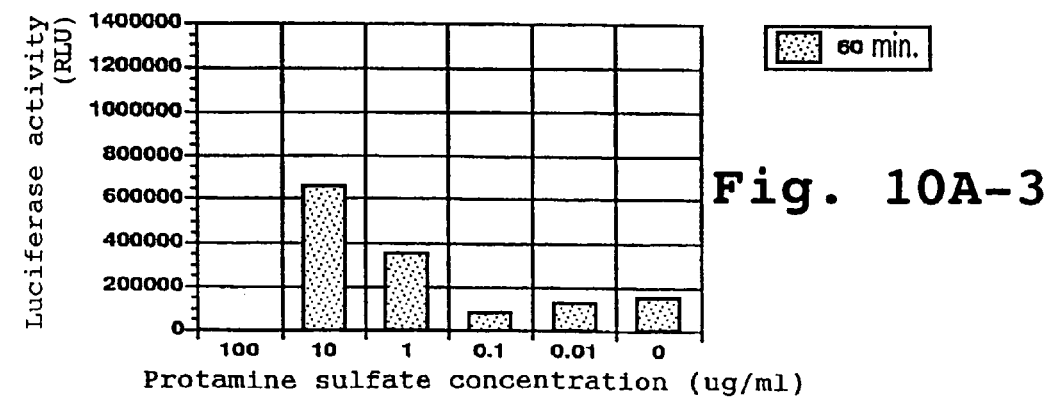
Figures 1, 10B:
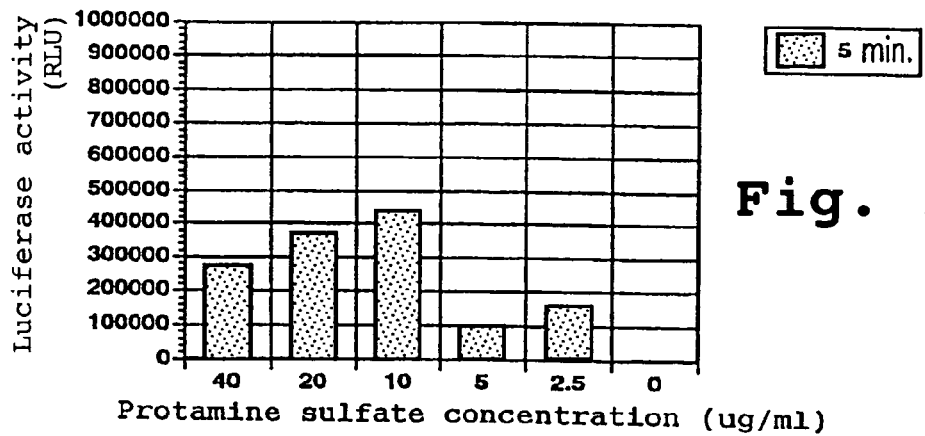
Figures 2, 10B:
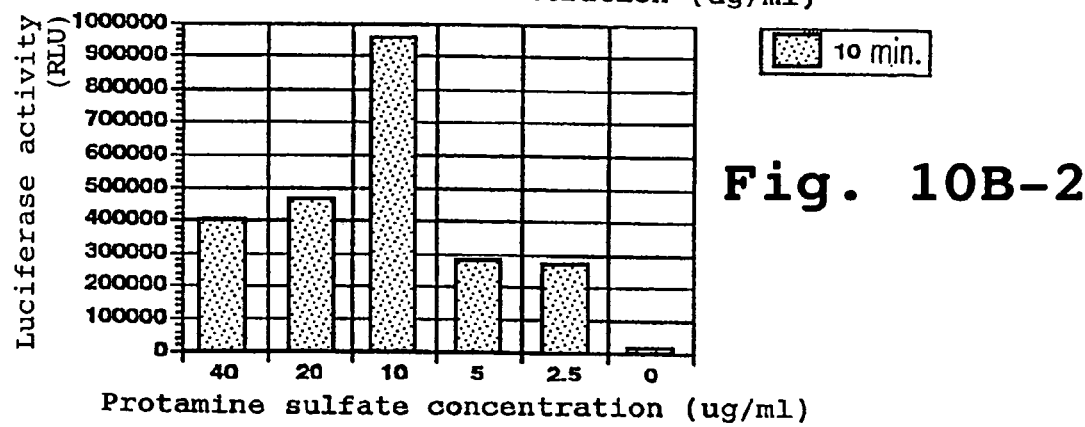
Figures 3, 10B:
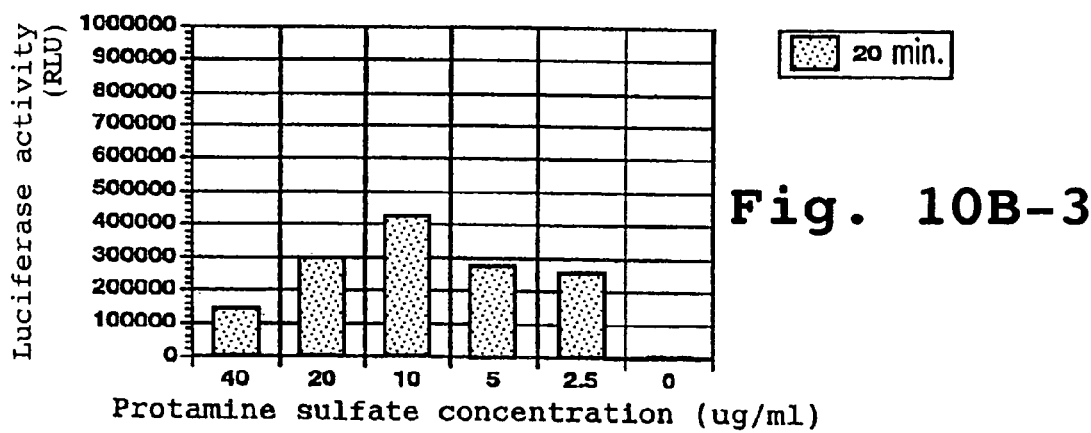
Figures 1, 11A:
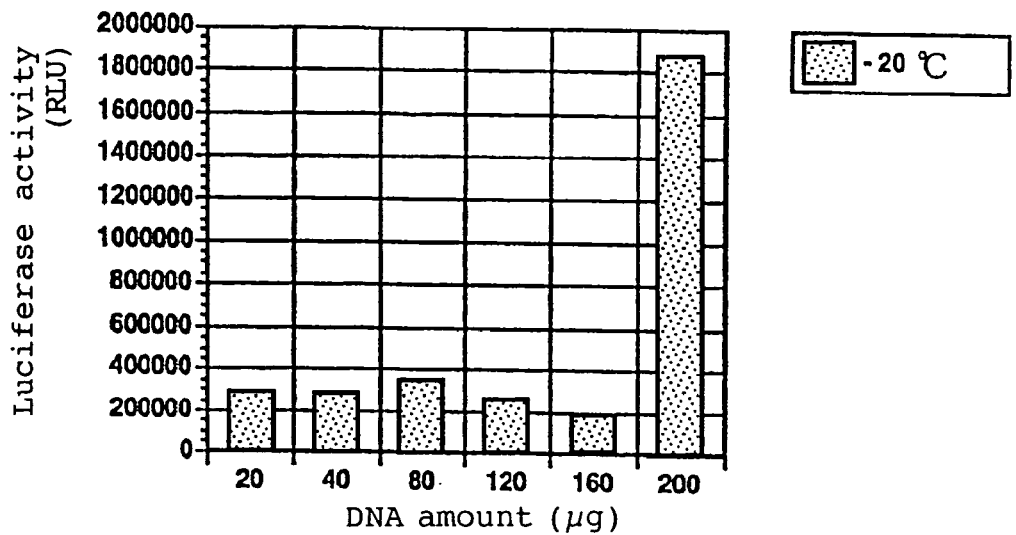
Figures 2, 11A:
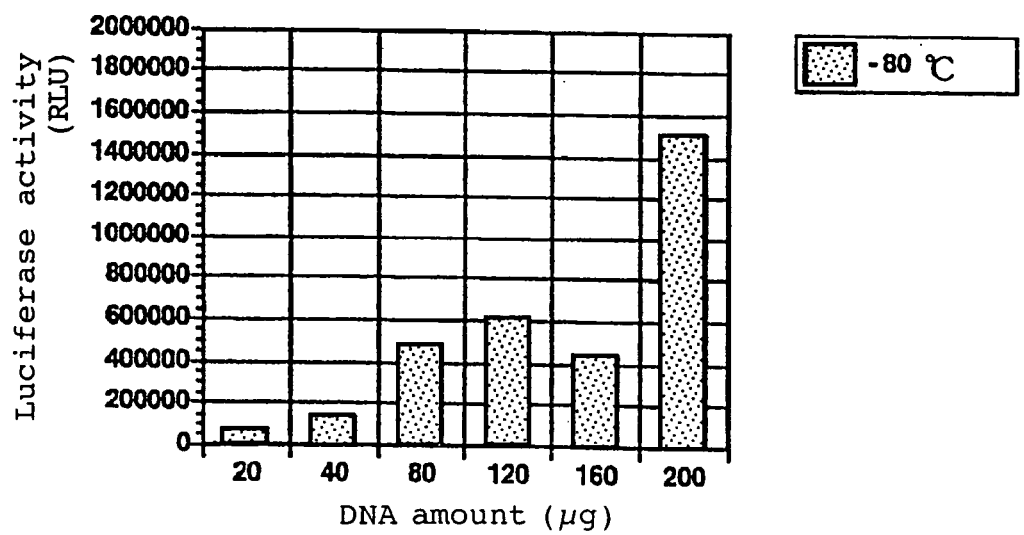
Figure 11B:
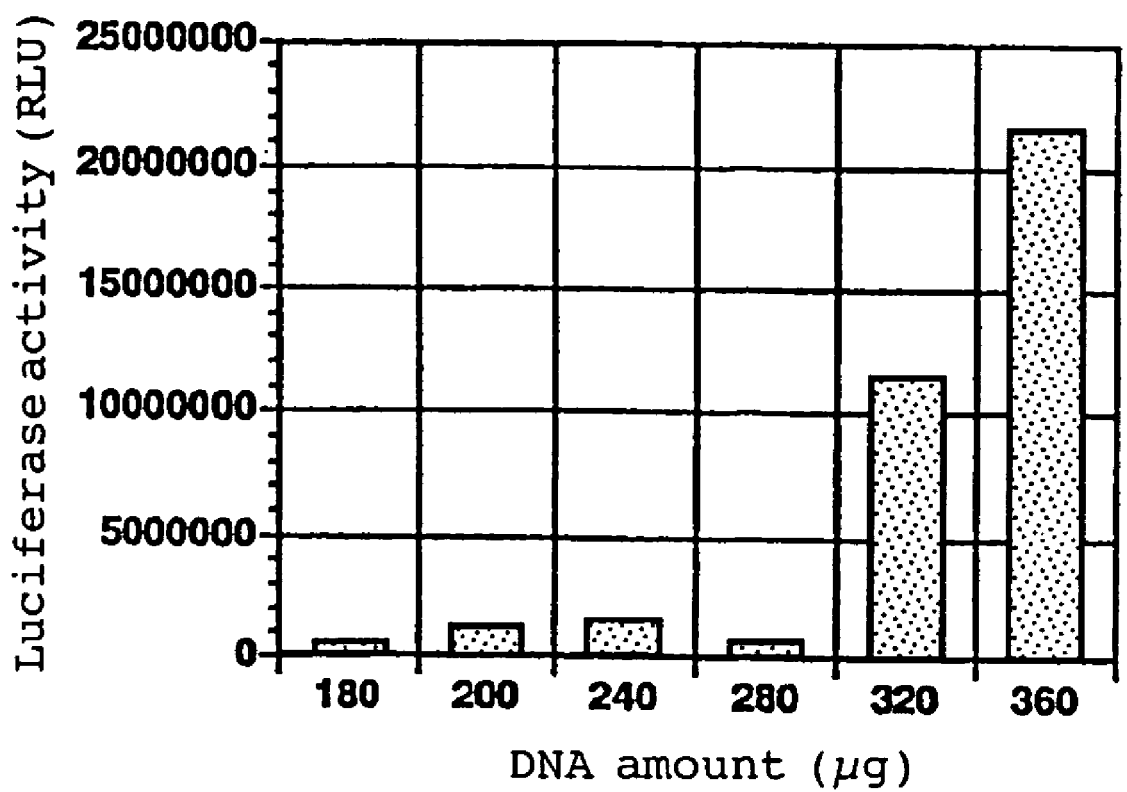

The results are shown in FIGS. 9A-9C.

(2.2: Conditions of Gene Transfer into Cells, Concentration/Treatment Time of Protamine Sulfate (PS))

The following modifications were made to the gene transfer method of (1) above, and the effects of protamine sulfate on the gene transfer via the HVJ envelope vector were examined;

(A) protamine sulfate: 0 to 100 μg/ml medium;
Transfection time: 20, 40, or 60 minutes.

(B) protamine sulfate 0 to 40 μg/ml medium;
Transfection time: 5, 10, or 20 minutes.

The results are shown in FIG. 10.

(2.3: Effects of Concentration of DNA Which is Encapsulated in the HVJ Envelope Vector on the Gene Expression Level)

The following modifications were made to the gene transfer method of (1), and the effects of the amount of DNA used for the experiment on the gene expression level via the HVJ envelope vector were examined:

(A) amount of DNA: 20 to 200 μg;

The HVJ envelope vector was stored at −20° C. or −80° C. for five days.

(B) amount of DNA: 180 to 360 μg/HVJ 10,000 HAU.

The results are shown in FIGS. 11A-1 to 11A-2 and 11B.

(2.4: Effects of Titer of HVJ Used for Gene Transfer on the Gene Expression Level)

The following modifications were made to the gene transfer method of (1), and the effects of the titer of HVJ used for gene transfer via the HVJ envelope vector on the gene expression amount was examined:

By using HVJ having a titer of 5,000, 10,000, or 20,000 HAU, HVJ envelope vectors were prepared, and BHK-21 cells were transfected with amounts thereof equivalent to 250, 500, 1,000, or 2,000 HAU.

Figure 12:
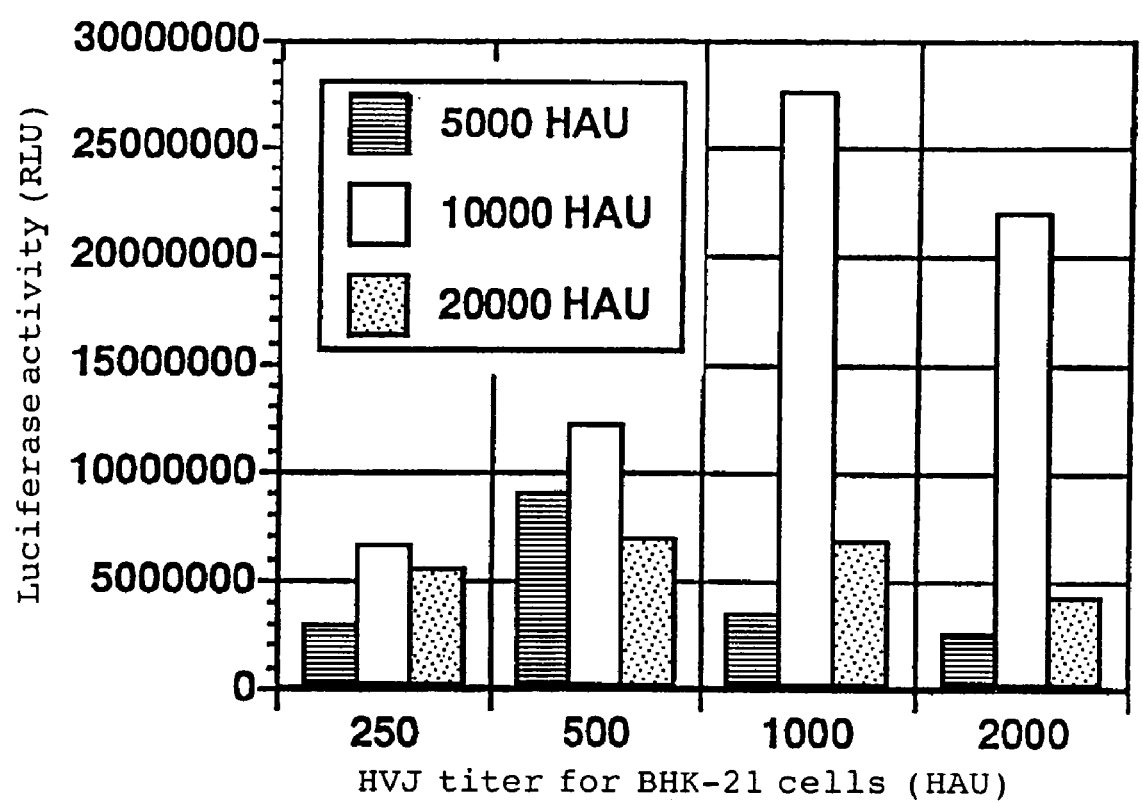
FIG. 12 is a graph representing gene transfer efficiency represented in terms of luciferase activity levels which were taken when HVJ envelope vectors were prepared by employing HVJ of various HAU titers and used for gene transfer, as shown in the figure.

The results are shown in FIG. 12.

(2.5: Effects of HVJ Inactivated Conditions on the HVJ Envelope Vector Gene Transfer Efficiency)

The following modifications were made to the gene transfer method of (1), and the effects of the HVJ inactivation method (UV or β-propiolactone) on the luciferase gene expression in BHK-21 cells were examined.

(A) irradiation amount used for UV inactivation: 0 to 231 $mJ/cm^2$.

(B) β-propiolactone (BPL) concentration used for HVJ treatment: 0 to 0.025%.

Figure 13A:
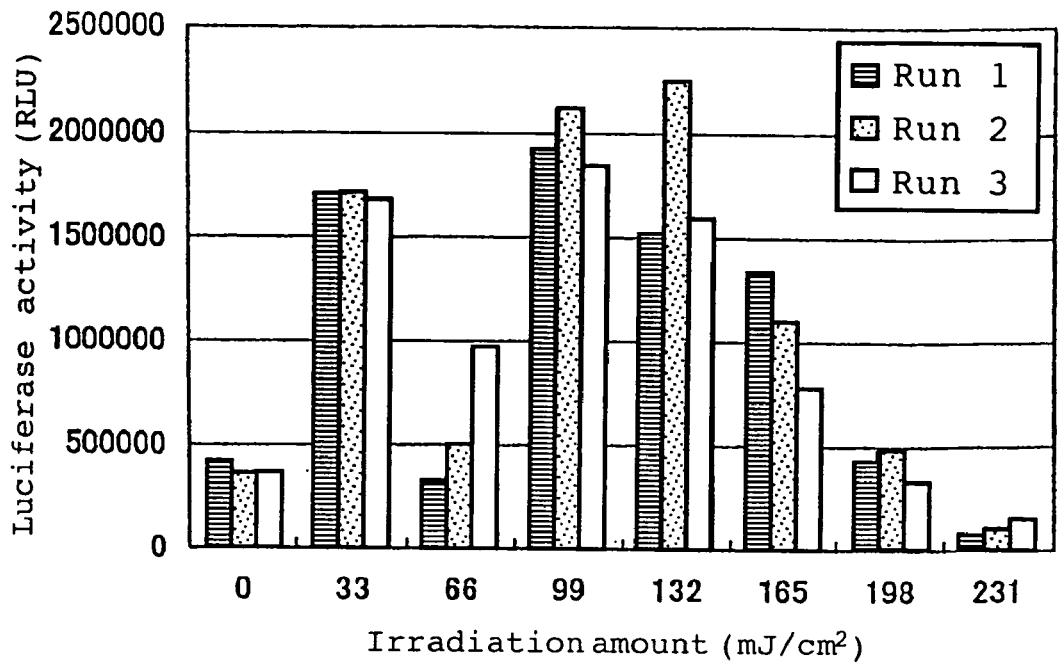
FIG. 13A is a graph representing gene transfer efficiency represented in terms of luciferase activity levels which were taken at the respective UV irradiation amounts as shown in the figure.
Figure 13B:
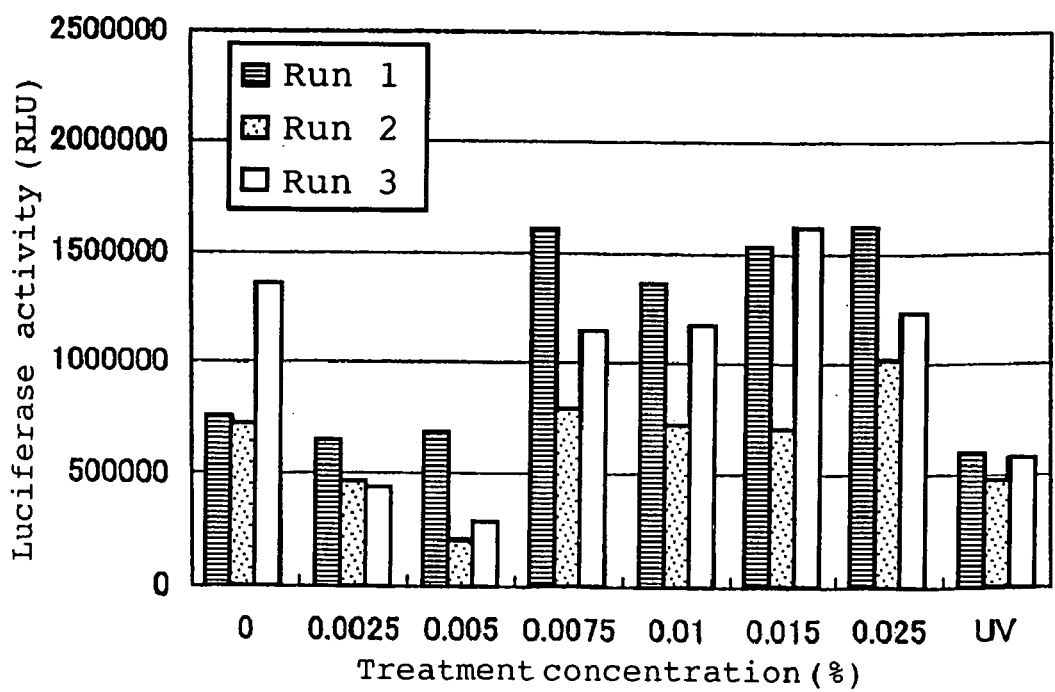
FIG. 13B is a graph representing gene transfer efficiency represented in terms of luciferase activity levels which were taken at the respective β-propiolactone (BRL) concentrations as shown in the figure.

The results are shown in FIGS. 13A and 13B. The samples were run in triplicate and each bar at each irradiation concentration corresponds to the sample tested in triplicate.

Example 12

Gene Transfer by the HVJ Envelope Vector into Various Cells

Figure 14:
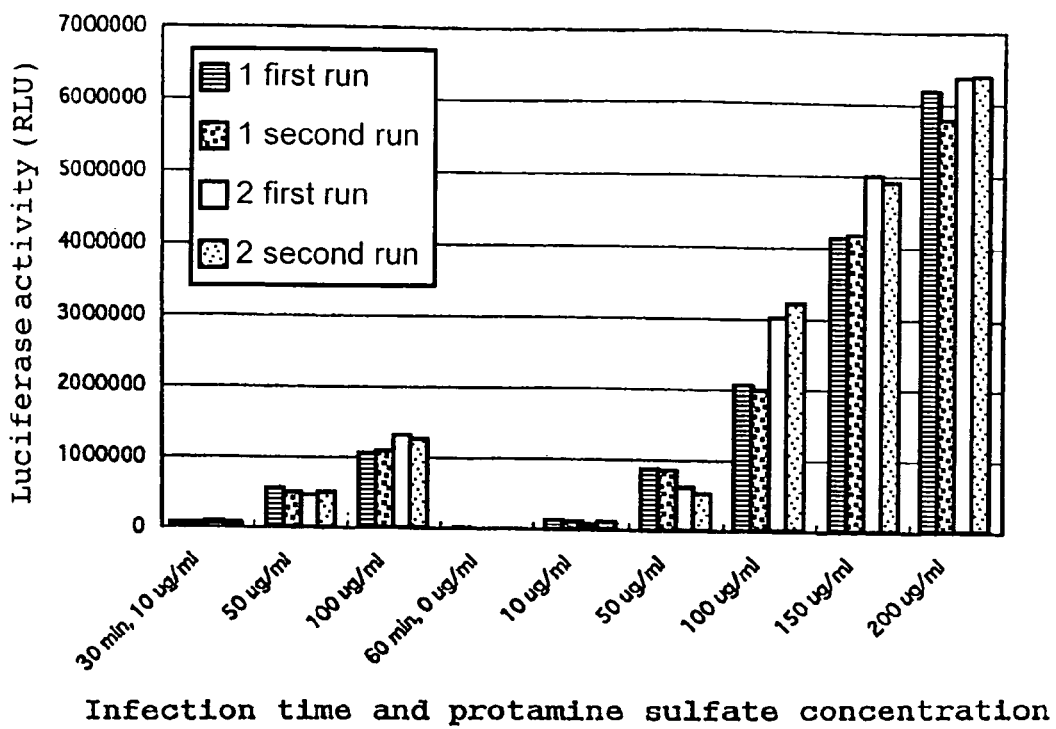
FIG. 14 is a graph representing gene transfer efficiency, for squamous cell carcinomas (SAS) on the human tongue, represented in terms of luciferase activity levels which were taken at the respective protamine sulfate concentration and the respective transfection incubation times, as shown in the figure.

To a squamous cell carcinoma (SAS) from a human tongue, gene transfer was performed in vitro according to the method described in Example 11. The results are shown in FIG. 14. The samples were run in duplicate and each bar at each protamine sulfate concentration and incubation time corresponds to the sample tested in duplicate. Upon gene transfer, the protamine sulfate concentration and the incubation time for transfection were varied as shown in FIG. 14, and the gene transfer efficiency was measured based on the expression of the luciferase gene. Under the conditions used for the transfection, the gene transfer efficiency was maximum in the case where a transfection treatment was carried out for 60 minutes by using 200 mg/ml of protamine sulfate. However, further increases in the gene transfer efficiency are expected by further increasing the protamine sulfate concentration.

Figure 15:
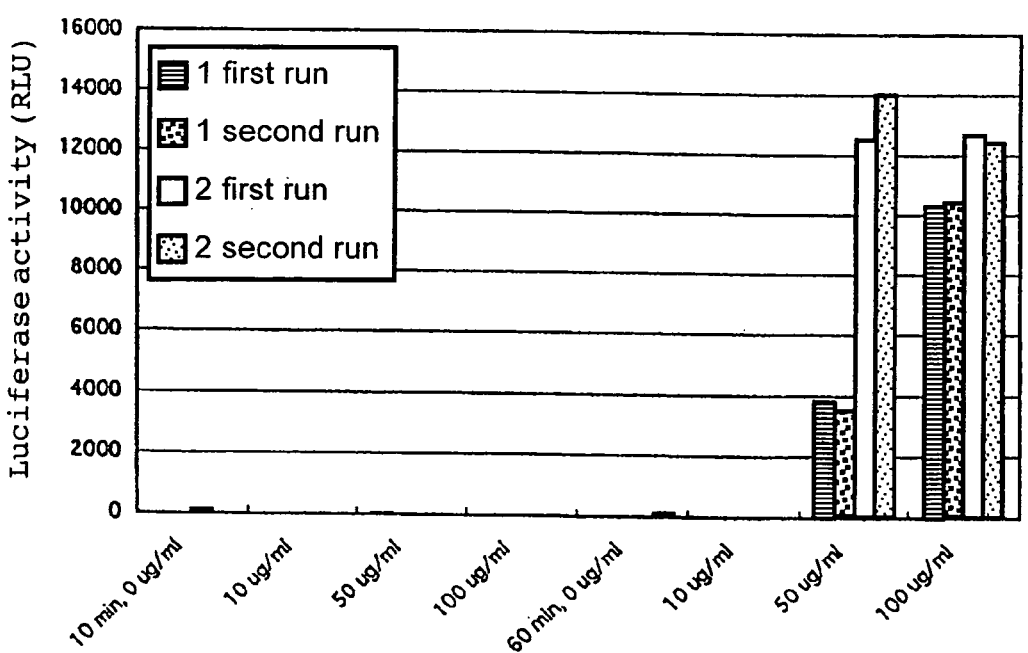
FIG. 15 is a graph representing gene transfer efficiency, for human aortic endothelial cells (HAEC), represented in terms of luciferase activity levels which were taken at the respective protamine sulfate concentration and the respective transfection incubation times, as shown in the figure.

Gene introduction was performed for human aortic endothelial cells (HAEC) according to the method described in Example 11. The results are shown in FIG. 15. The samples were run in duplicate and each bar at each protamine sulfate concentration and incubation time corresponds to the sample tested in duplicate.

Upon gene transfer, the protamine sulfate concentration and the incubation time for transfection were varied as shown in FIG. 15, and the gene transfer efficiency was measured based on the expression of the luciferase gene. Under the conditions used for the transfection, the gene transfer efficiency was maximum in the case where a transfection treatment was carried out for 60 minutes by using 100 µg/ml of protamine sulfate. However, further increases in the gene transfer efficiency are expected by further increasing the protamine sulfate concentration.

Example 13

Gene Transfer by the HVJ Envelope Vector into Various Types of In vivo Tissue

The present example illustrates examples of gene transfer into various types of in vivo tissue employing the HVJ envelope vector described in Example 11.

(13.1: Mouse Liver)

An HVJ envelope vector was prepared by leaving 0.8% octylglucoside with 200 µg pcLuci on ice for 1 minute, which was suspended in 300 µl of PBS. One-tenth, 30 µl, (equivalent to 1,000 HAU) of the prepared suspension was diluted with 70 µl of PBS (total amount: 100 µl) and the diluted solution was injected into one lobe of a mouse (C57BL/6) liver.

An HVJ-AVE (Artificial Viral Envelope) liposome was prepared by vortexing/extrusion with 200 µg pcLuci followed by sucrose gradient centrifugation (62000 g, 90 minutes). Then the preparation was pelleted down by centrifugation (27000 g, 30 minutes) and the pellet was suspended in 500 µl of PBS. One hundred microliters of the sample was injected into one lobe of a mouse (C57BL/6) liver.

Twenty-four hours later, the liver lobe after injection was isolated and the luciferase activity of the lobe was assayed using Luciferase Assay System (Promega). The results are shown in FIG. 16A. As is clear from these results, the HVJ envelope vector according to the present invention showed a remarkably high gene transfer efficiency which was about twice as high as that of conventional HVJ-AVE liposome.

(13.2: Mouse Uterus)

An HVJ envelope vector was prepared as described in 13.1. Fifty microliters and one hundred microliters of the sample was diluted with PBS to 500 µl, was infused into a Fallopian tube of a mouse and the cervix was ligated for 10 minutes. Twenty-four hours later, the mouse uterus was isolated and the luciferase activity of the lobe or uterus was assayed using Luciferase Assay System (Promega). The results are shown in FIG. 16B. While the HVJ envelope vector according to the present invention enabled gene transfer into the mouse uterus, the method employing HVJ-AVE liposome did not exhibit a detectable level of gene transfer into the uterus tissue.

An HVJ envelope vector containing pcLuci was prepared as described in 13.1. For LacZ expression, an HVJ envelope vector containing pEB-CMV-LacZ (13 kb) was prepared using 200 µg of the plasmid. HVJ envelope vectors containing these vectors were injected into the uterus as described above. The results are shown in FIG. 16C. Through LacZ staining, expression of the LacZ gene was detected chiefly in the glandular epithelium of the endometrium.

An HVJ envelope vector containing pEGFP-1 (i.e., a vector where a green fluorescence protein gene (about 0.7kb) of jellyfish is incorporated into an expression vector having a cytomegalovirus promoter; available from Clontech, Palo Alto, Calif.) was prepared by a method similar to the aforementioned method for preparing an HVJ envelope vector containing pcLuci. Thirty microliters of the vector (equivalent to 1000HAU, 1/10 of the preparation) was injected into either the carotid artery or the intrathecal space via the cisterna magna of SD rats (Sprague-Dawley rats). Three to four days after the gene transfer, the rats were sacrificed, and brain sections were prepared without fixation. Fluorescence was observed under fluorescence microscopy. As indicated by the results shown in FIGS. 16D-1 to 16D-3, intracerebral expression of green fluorescence protein (GFP) was observed with both injection into the carotid artery and injection into the intrathecal space via the cisterna magna. On the other hand, intracerebral GFP expression was not observed when a similar gene transfer was performed via the rat carotid artery by using HVJ-AVE liposome.

(13.4: Rabbit Eye)

pCMV-NK4, which was constructed by cloning NK4 cDNA (1.4 kb), a mutant of the human HGF (hepatocyte growth factor) gene at the HindIII/XbaI site of pCDNA3 (In Vitrogen, San Diego, Calif.) was kindly donated by Professor Toshikazu NAKAMURA et al. of Osaka University, Graduate School of Medicine.

An HVJ envelope vector was prepared by a method similar to the aforementioned method for preparing an HVJ envelope vector containing pcLuci except that either 400 or 800 µg of pCMV-NK4 was used with inactivated HVJ of 10000 HAU. pCMV-NK4 is a vector which expresses a mutant HGF which inhibits the HGF function. Fifty microliters of the vector (1/6 of the preparation) was injected into rabbit corneal tissue which was treated with a pellet of recombinant VEGF to induce angiogenesis. Seven days after treatment, the rabbits were sacrificed and angiogenesis in the eye was observed. The results are shown in FIG. 16E. pCMV-NK4 suppressed angiogenesis induced by VEGF in a dose-dependant manner.

(13.5: Rat Pulmonary Artery)

An HVJ envelope vector containing pSV-LacZ (Promega, Madison, Wis.) having a LacZ gene under the control of SV40 promoter was prepared by a method similar to the aforementioned method for preparing an HVJ envelope vector containing pcLuci. Fifty microliters of the vector (1/6 of the preparation) was injected into a rat trachea. Three days after the gene transfer, the rats were sacrificed, and the expression of LacZ in the artery was visualized with X-gal after fixation of the tissue with 1% glutaraldehyde. The results are shown in FIG. 16F. Gene expression was observed in the bronchial epithelium also in the case where the HVJ envelope vector was introduced via the pulmonary artery (data not shown).

Example 14

Functions of a Virus Envelope Vector as a Drug Delivery System (DDS)

The gene transfer vector according to the present invention is also useful as a drug delivery system for oligonucleotides or decoy nucleic acid therapy.

(14.1: Introduction of Fluorescent Oligonucleotides)

By employing the virus envelope vector according to the present invention, fluorescence-labeled oligonucleotides were introduced into cells.

Figures 1, 17B:
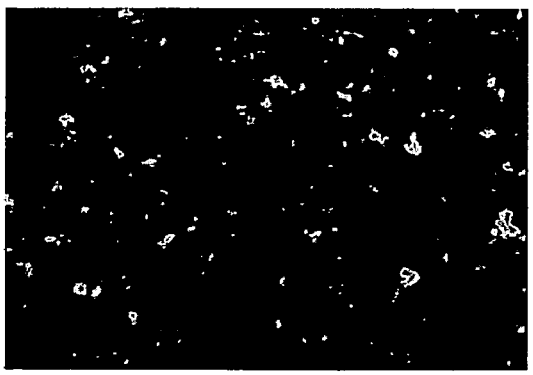
Figures 2, 17B:
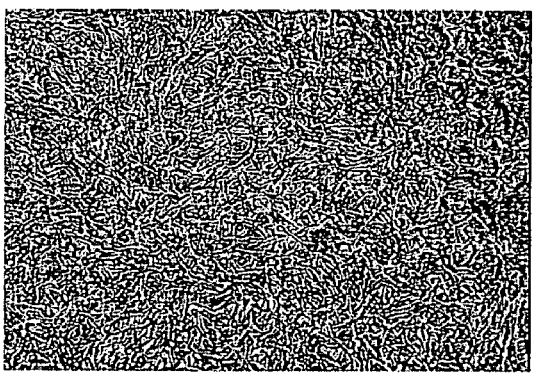

Twenty-mer oligonucleotides (5'-CCTTgAAGG-GATTTCCCTCC-3')(SEQ ID NO: 1)(194µg/92µl of BSS), which were labeled at the 5' position with FITC, were mixed with a precipitate of HVJ of 10,000 HAU (which had been inactivated with 198mJ/cm$^2$ of UV light). Triton X-100 (final concentrations 0.24%) was added, and the mixture was subjected to a treatment on ice for 1 minute. One milliliter of BSS was added, and the mixture was centrifuged (15,000 rpm, 15 minutes, 4° C.). To the precipitate, 100 µl of PBS was added, and the mixture was stored at −20° C. One month later, the mixture was thawed, and 10 µl thereof was mixed with 5 µg of protamine sulfate, and incubated (10 minutes, 60 minutes) with 5,000,000 BHK-21cells (in a 0.5 ml of medium). On the next day of the introduction, the cell fluorescence was observed under fluorescence microscopy. As a result, about 10% oligonucleotide introduction efficiency was obtained after 10 minutes as shown in FIGS. 17B-1 and 17B-2, whereas the oligonucleotides were introduced into 80% or more of the cells after 60 minutes as shown in FIGS. 17A-1 and 17A-2.

(14.2: Therapy for Contact Dermatitis Using Stat6 Decoy Nucleic Acids)

By employing the virus envelope vector according to the present invention, decoy nucleic acids were introduced into cells.

Double-strand nucleic acids having a Stat6 DNA binding sequence (5'-GATCAAGACCTTTTCCCAAGAATCTAT-3' (SEQ ID NO: 2) and 3'-CATGTTCTGGAAAAGGGTTCT-TAGATA-5' (SEQ ID NO: 3), (Wang, L. H. et al.: Blood 95, 1249 to 1257, 2000))(250 µg/300 µl of BSS) were mixed with a precipitate of HVJ of 30,000 HAU (which had been inactivated with 99 mJ/cm$^2$ of UV light).

Triton X-100 (final concentration: 0.24%) was added, and the mixture was subjected to a treatment on ice for 1 minute. One milliliter of BSS was added, and the mixture was centrifuged (15,000 rpm, 15 minutes, 4%). To the precipitate, 300 µl of PBS was added, and the mixture was stored at −20%. This HVJ envelope vector was used for subcutaneous injection into mice, which led to the suppression of an IgE-induced allergy and delayed cutireaction.

Example 15

Gene Transfer to Suspension Cells

Using CCRF-CEM, NALM-6. K-562, which resemble human leukemia cells, a gene transfer experiment was conducted.

Two hundred micrograms of pCMV-Luciferase (92 µl) was mixed with a precipitate of inactivated HVJ (UV light 99 mJ/cm$^2$) of 10,000 HAU.

Triton X-100 (final concentrations 0.24%) was added, and the mixture was subjected to a treatment on ice for 1 minute. One milliliter of BSS was added, and the mixture was centrifuged (15,000 rpm, 15 minutes, 4). To the precipitate, 300 µl of PBS was added, whereby an HVJ envelope vector was prepared. Sixty microliters of the vector (equivalent to 2,000 HAU), protamine sulfate, and 4.000,000 suspension cells were mixed in a 1.5 ml Eppendorf tube, and was subjected to a centrifugation (10,000 to 15,000 rpm, 10 minutes, 20° C.). Thereafter, a culture solution was added to the precipitate, and the mixture was placed on a culture dish. One day later, the luciferase activity of the cells was measured.

The cell lines used (in particular CCRF-CEM and NALM-6) show a very low introduction efficiency in the case where HVJ-liposomes or existing liposome reagents (Lipofectamine, Lipofectin of Gibco BRL, etc.) are used. However, as shown in FIGS. 18A to 18C, a highly efficient gene transfer to these cell lines was observed. The samples were run in duplicate and each bar at each protamine sulfate concentration and centrifugation rpm corresponds to the sample tested in duplicate.

The preferable gene transfer conditions were determined to be the following conditions: addition of 600 to 1,000 µg/ml of protamine sulfate and a centrifugation at 10,000 rpm or 15,000 rpm, for 10 minutes at 20° C. No significant cytotoxicity associated with the HVJ envelope vector was observed. Both centrifugation and the addition of protamine sulfate were required for the gene transfer Example 16

Gene Transfer to Cancerous Tissue

Three hundred fifty-four micrograms of pCMV-Luciferase (92 µl) was mixed with a precipitate of inactivated HVJ (UV light 99 mJ/cm$^2$) of 34,000 HAU. Triton X-100 (final concentration: 0.24%) was added, and the mixture was subjected to a treatment on ice for 1 minute. One milliliter of BSS was added, and the mixture was centrifuged (10,000 to 15,000 rpm, 10 minutes, 20° C.). To the precipitate, 300 µl of PBS was added, and the mixture was stored at −20° C. One day later, the mixture was mixed with 500 µg/ml or 1000 µg/ml of protamine sulfate. One hundred microliters thereof was injected into a tumor mass of mouse melanoma B16-F1 (diameter: 7 to 8 mm). One day later, the luciferase activity was measured. As shown in FIG. 19, gene expression was observed in the tumor mass. The preferable protamine sulfate concentration was 500 µg/ml. On the other hand, gene expression was not detectable at lower protamine sulfate concentrations.

Example 17

Preparation of Herpes Virus Envelope Vectors (17.1: Preparation of Inactivated Virus)

Herpes simplex virus type 1 (HSV-1)(10$^{10}$ plaque formation units/ml) was kindly donated by Professor Yamanishi of Osaka University, Graduate School of Medicine, Department of Bacteriology. The inactivation conditions for this virus were examined based on the viral plaque formation in cultured simian cells (Vero cells). When the virus was inactivated with β-propiolactone (BPL) 0.05%, the plaque appeared in Vero cells at a frequency of 9.1×10$^{-4}$ (plaque/Vero cell). On the other hand, when the virus was inactivated by the irradiation of 200 or 400 mJ/cm$^2$ of UV light, the frequencies was 4.3×10$^{-4}$ or 2.2×10$^{-4}$ (plaque/Vero cell), respectively.

(17.2: Gene Transfer Employing Inactivated Virus)

After 100 µl of HSV-1 (10$^9$ particles) was diluted with 620 µl of PBS, the diluted solution was irradiated with 400 mJ/cm$^2$ of UV light. Ten percent thereof (72 µl) was mixed with DNA (pCMV-Luciferase 8.83 µg/µl). Eight microliters of 3% Triton X-100 (final concentration: 0.24%) was added, and 1 ml of PBS was added 1, 2, 3, 4, 5, or 6 minutes later, thereby diluting the solution. One hundred microliters of each sample was introduced, with further treatment, into BHK-21 cells (in a 6 well plate). The cells were cultured in Dulbecco minimum essential medium (DME)(0.5 ml/well) containing 10% fetal calf serum (FCS). In another experiment, 100 µl of each sample was mixed with 5 µg of protamine sulfate, which was thereafter introduced in BHK-21. After the samples were left in an incubator (37° C., 5% CO$_2$) for 60 minutes, the culture solution was replaced by 10% FCS-DME. The luciferase activity was measured 22 hours later. As shown in FIG. 20, a highly efficient gene transfer by the herpes virus envelope vector which was prepared by the method according to the present invention was confirmed. None of the samples showed any cytotoxicity through a morphological observation.

Next, after a herpes virus envelope vector which was treated with Triton-X100 for 5 minutes was stored at −80% for two days, the vector was thawed and again added to BHK-21 cells, and the introduction efficiency was measured. This time, 10% FCS-DME (2.5 ml/well) was added in 60 minutes from the introduction and cultured overnight, and then the activity was measured. The effects of the serum and amounts of the vector were studied.

As shown in FIG. 21, a highly efficient gene transfer was confirmed even after two days of storage at −80° C. A higher introduction efficiency was shown with the medium to which 10% serum was added than with the serum-free medium. A higher gene transfer activity was shown with 200 µl of the vector solution (estimated amount: $2.8 \times 10^7$ virus particles/well) than with 100 µl of the solution (estimated amount: $1.4 \times 10^7$ virus particles/well).

(17.3: Gene Transfer Employing Inactivated Virus)

From the above disclosure, it would be clear to those skilled in the art that the present technique of creating an envelope vector by employing a detergent is applicable not only to HVJ but also to a broad range of envelope viruses which have lipid membranes. Accordingly, it is evident that those skilled in the art can easily prepare envelope vectors for gene transfer by employing any other envelope viruses, in accordance with the disclosure of the present invention. Hence, an envelope vector using a virus of Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae, Hepadnaviridae, etc., can be created. Accordingly, it is contemplated that introduction of a target into specific organs can be realized by utilizing the tissue directivity of viruses. For example, an envelope vector using herpes simplex virus would be applicable as a nerve-directed vector; an envelope vector using Epstein-Barr virus would be applicable as a B lymphocyte-directed vector: and an envelope vector using influenza would be applicable as a respiratory organ-directed vector.

Thus, specific embodiments of the present invention are described in the present specification with respect to illustrative objectives. However, it should be clear that various modifications may be made without departing from the spirit and scope of the present invention. Specifically, while the examples in the present specification are described with respect to gene transfer vectors employing inactivated HVJ, it should be clear to those skilled in the art based on the disclosure in the present specification that a gene transfer vector according to the present invention can be prepared by inactivating virus other than HVJ, and that a gene transfer vector according to the present invention can be prepared without an inactivation step, by employing a similar preparation method. Accordingly, the present invention is limited only by the attached claims.

INDUSTRIAL APPLICABILITY

A novel gene transfer method is provided which permits simple operation and yet provides an excellent gene transfer efficiency. It is contemplated that this enables a quick screening of gene libraries. There is also provided a high throughput screening kit which contains the virus envelope vector according to the present invention. Moreover, the virus envelope vector provided according to the present application can accept a long period of frozen storage, so that it does not need to be prepared upon use. As a result, the operational process can be greatly simplified, and a uniform gene transfer based on mass-produced introduction vectors can be realized. Furthermore, the gene transfer vector according to the present invention enables a more efficient gene transfer than any conventional vectors which are prepared based on HVJ, and enables gene transfer into a broader range of in vivo tissue than do conventional methods.

There are also provided drug delivery systems for the administration of medical drugs, drug screening systems, and vectors for gene therapy which contain the gene transfer vector according to the present invention.

The invention claimed is:

1. A method of introducing an exogenous gene into animal tissue in vivo, comprising:
   (a) providing an encapsulated gene transfer vector comprising a non-liposomal viral envelope from inactivated virus articles having F and HN membrane proteins and an exogenous gene;
   (b) subjecting the encapsulated gene transfer vector to at least five cycles of freezing then thawing; and
   (c) introducing into the animal tissue the encapsulated gene transfer vector to achieve introduction of the exogenous gene into the animal tissue.

2. The method according to claim 1, wherein the tissue into which the encapsulated gene transfer vector is introduced is selected from the group consisting of liver, skeletal muscle, uterus, brain, eyes, carotid arteries, skin, blood vessels, lung, heart, kidneys, spleen, cancer tissue, nerves, B lymphocytes, and respiratory tract tissue.

3. The method according to claim 1, further comprising purifying a virus to obtain the non-liposomal viral envelope provided in the encapsulated gene transfer vector of step (a).

4. The method according to claim 3, wherein the purification step comprises:
   (a) centrifugation of the virus in a fixed-angle rotor.

5. The method according to claim 3, wherein the purification step comprises:
   (a) centrifugation of the virus in a fixed-angle rotor at about 27,000 g.

6. The method according to claim 1, further comprising encapsulating the exogenous gene within the non-liposomal viral envelope from inactivated virus particles having F and HN membrane proteins in the presence of a detergent selected from the group consisting of octylglucoside, Triton-X100, CHAPS, and NP-40 to obtain the encapsulated gene transfer vector of step (a).

7. The method according to claim 6, wherein the detergent is octylglucoside.

8. The method of claim 1, wherein the non-liposomal viral envelope is a Sendai virus envelope.

9. An encapsulated gene transfer vector for introducing an exogenous gene into animal tissue in vivo, comprising a non-liposomal viral envelope from inactivated virus particles having F and HN membrane proteins and an exogenous gene,
   wherein the non-liposomal viral envelope is selected from a Sendai virus envelope; and
   wherein the encapsulated gene transfer vector has been subjected to at least five cycles of freezing then thawing.

10. The vector of claim 9, wherein the mixture is subjected to about ten cycles of freezing then thawing.

11. The vector of claim 9, wherein the mixture is subjected to about fifteen cycles of freezing then thawing.

12. The vector of claim 9, wherein the mixture is subjected to about twenty cycles of freezing then thawing.

13. The method of claim 1, wherein the mixture is subjected to about ten cycles of freezing then thawing.

14. The method of claim 1, wherein the mixture is subjected to about fifteen cycles of freezing then thawing.

15. The method of claim 1, wherein the mixture is subjected to about twenty cycles of freezing then thawing.

16. The method of claim 1, wherein the encapsulated gene transfer vector achieves a higher level of expression of the exogenous gene than an identical encapsulated gene transfer vector which has not been subjected to at least five cycles of freezing then thawing.

17. The vector of claim 9, which achieves a higher level of expression of the exogenous gene than an identical encapsulated gene transfer vector which has not been subjected to at least five cycles of freezing then thawing.

\* \* \* \* \*